US012685584B2

(12) United States Patent
Marchand et al.

(10) Patent No.: US 12,685,584 B2
(45) Date of Patent: Jul. 21, 2026

(54) INSTRUMENT PORT FOR EPICARDIAL ABLATION WITH ANATOMICAL EPICARDIAL STRUCTURES AND REAL-TIME LESION IMAGE PROCESSOR

(71) Applicant: CIRCA SCIENTIFIC, INC., Englewood, CO (US)

(72) Inventors: Thomas Marchand, Boston, MA (US); Jonathan B. O'Keefe, North Attleboro, MA (US)

(73) Assignee: Circa Scientific, Inc., Englewood, CO (US)

( * ) Notice: Subject to any disclaimer, the term of this patent is extended or adjusted under 35 U.S.C. 154(b) by 501 days.

(21) Appl. No.: 16/951,903

(22) Filed: Nov. 18, 2020

(65) Prior Publication Data

US 2021/0145511 A1     May 20, 2021

Related U.S. Application Data

(60) Provisional application No. 63/076,075, filed on Sep. 9, 2020, provisional application No. 62/936,736, filed on Nov. 18, 2019.

(51) Int. Cl.
*A61B 18/14*          (2006.01)
*A61B 1/00*          (2006.01)
(Continued)

(52) U.S. Cl.
CPC .... *A61B 18/1492* (2013.01); *A61B 1/000094* (2022.02); *A61B 1/00082* (2013.01);
(Continued)

(58) Field of Classification Search
CPC ........... A61B 18/1492; A61B 1/00082; A61B 1/0011; A61B 1/00128; A61B 1/0052;
(Continued)

(56) References Cited

U.S. PATENT DOCUMENTS 2,243,992 A     6/1941  Wappler
2,767,705 A     10/1956  Moore
(Continued)

FOREIGN PATENT DOCUMENTS

JP     2001517528 A     10/2001
JP     2014239739 A     12/2014
(Continued)

OTHER PUBLICATIONS

International Search Report & Written Opinion, PCT/US07/00270, Oct. 1, 2007.
(Continued)

*Primary Examiner* — Thomas A Giuliani
*Assistant Examiner* — Abigail M Ziegler
(74) *Attorney, Agent, or Firm* — Bochner PLLC; Andrew D. Bochner; Ross Brown

(57)          ABSTRACT

A method for controlling an epicardial ablation procedure comprises (a) inserting an instrument port comprising an ablation tool, an optical camera and an optical light emitter into an epicardial cavity proximal to a target region; (b) providing optical light into said epicardial cavity through said optical light emitter to illuminate said target region; (c) obtaining a first image of said target region using said optical camera; (d) steering a tip of said ablation tool towards said target region; (e) applying an ablation energy to said target region using the ablation tool so as to form a lesion in or on said target region; (f) obtaining a second image of said target region using said optical camera; and (g) processing at least one of said first and second images in an image processor so as to determine a characteristic of said lesion.

20 Claims, 28 Drawing Sheets

(51) Int. Cl.

| | |
|---|---|
| *A61B 1/005* | (2006.01) |
| *A61B 1/015* | (2006.01) |
| *A61B 1/018* | (2006.01) |
| *A61B 1/06* | (2006.01) |
| *A61L 29/02* | (2006.01) |
| *A61M 25/00* | (2006.01) |
| *A61M 25/01* | (2006.01) |
| *A61M 25/10* | (2013.01) |
| *A61B 1/05* | (2006.01) |
| *A61B 18/00* | (2006.01) |

(52) U.S. Cl.

CPC ........ *A61B 1/0011* (2013.01); *A61B 1/00128* (2013.01); *A61B 1/00148* (2022.02); *A61B 1/0052* (2013.01); *A61B 1/0056* (2013.01); *A61B 1/015* (2013.01); *A61B 1/018* (2013.01); *A61B 1/0676* (2013.01); *A61L 29/02* (2013.01); *A61M 25/0043* (2013.01); *A61M 25/005* (2013.01); *A61M 25/0054* (2013.01); *A61M 25/0136* (2013.01); *A61M 25/0147* (2013.01); *A61M 25/1002* (2013.01); *A61B 1/05* (2013.01); *A61B 1/0646* (2013.01); *A61B 1/0661* (2013.01); *A61B 2018/0022* (2013.01); *A61B 2018/00363* (2013.01); *A61B 2018/00577* (2013.01); *A61B 2018/00696* (2013.01); *A61B 2018/00982* (2013.01); *A61B 2218/002* (2013.01); *A61B 2218/007* (2013.01); *A61M 25/0013* (2013.01)

(58) Field of Classification Search

CPC ....... A61B 1/0056; A61B 1/015; A61B 1/018; A61B 1/0676; A61B 1/05; A61B 2018/0022; A61B 2018/00363; A61B 2018/00577; A61B 2018/00696; A61B 2018/00982; A61L 29/02; A61M 25/0043; A61M 25/0136; A61M 25/0147; A61M 25/1002; A61M 25/0013; A61M 25/005; A61M 25/0054

See application file for complete search history.

(56) References Cited

U.S. PATENT DOCUMENTS

| | | | |
|---|---|---|---|
| 4,201,199 A | 5/1980 | Smith | |
| 4,233,982 A | 11/1980 | Bauer et al. | |
| 4,535,773 A | 8/1985 | Yoon | |
| 5,195,955 A | 3/1993 | Michael | |
| 5,441,503 A | 8/1995 | Considine et al. | |
| 5,722,402 A | 3/1998 | Swanson et al. | |
| 5,797,960 A | 8/1998 | Stevens et al. | |
| 5,842,971 A | 12/1998 | Yoon | |
| 5,848,966 A | 12/1998 | Undquist et al. | |
| 5,899,915 A | 5/1999 | Saadat | |
| 5,928,218 A | 7/1999 | Gelbfish | |
| 6,033,426 A | 3/2000 | Kaji | |
| 6,129,713 A | 10/2000 | Mangosong et al. | |
| 6,178,346 B1 | 1/2001 | Amundson et al. | |
| 6,238,389 B1 | 5/2001 | Paddock et al. | |
| 6,293,282 B1 | 9/2001 | Lemelson | |
| 6,309,345 B1 | 10/2001 | Stelzer et al. | |
| 6,554,793 B1 | 4/2003 | Pauker et al. | |
| 6,641,562 B1 | 11/2003 | Peterson | |
| 6,689,085 B1 | 2/2004 | Rubenstein et al. | |
| 8,394,015 B2 | 3/2013 | Dibiasio et al. | |
| 8,758,228 B2 | 6/2014 | Saadat et al. | |
| 8,951,275 B2 | 2/2015 | Cannon et al. | |
| 9,314,263 B2 | 4/2016 | Escudero et al. | |
| 2001/0016725 A1 | 8/2001 | Valley et al. | |
| 2002/0026094 A1 | 2/2002 | Roth | |
| 2002/0111585 A1 | 8/2002 | LaFontaine | |
| 2002/0161378 A1 | 10/2002 | Downing | |
| 2003/0149422 A1* | 8/2003 | Muller | A61M 25/0136 604/528 |
| 2004/0024414 A1 | 2/2004 | Downing | |
| 2004/0111019 A1 | 6/2004 | Long | |
| 2004/0116897 A1 | 6/2004 | Aboul-Hosn | |
| 2004/0193191 A1 | 9/2004 | Starksen et al. | |
| 2004/0199052 A1 | 10/2004 | Banik et al. | |
| 2005/0234296 A1 | 10/2005 | Saadat et al. | |
| 2005/0234298 A1 | 10/2005 | Kucklick et al. | |
| 2007/0197896 A1 | 8/2007 | Moll et al. | |
| 2009/0036744 A1 | 2/2009 | Vayser | |
| 2009/0275893 A1 | 11/2009 | Dibiasio et al. | |
| 2010/0130836 A1* | 5/2010 | Malchano | A61B 5/6852 600/407 |
| 2010/0211006 A1* | 8/2010 | Schmidt-Sorensen | A61M 25/09041 604/95.01 |
| 2012/0239028 A1 | 9/2012 | Wallace et al. | |
| 2012/0289858 A1 | 11/2012 | Ouyang et al. | |
| 2013/0165908 A1 | 6/2013 | Purdy et al. | |
| 2013/0245371 A1 | 9/2013 | Mourlas et al. | |
| 2013/0296780 A1 | 11/2013 | Tegg | |
| 2013/0324973 A1* | 12/2013 | Reed | A61M 25/0097 604/528 |
| 2014/0012155 A1* | 1/2014 | Flaherty | A61B 5/0086 600/549 |
| 2015/0196202 A1 | 7/2015 | Mercader et al. | |
| 2015/0320481 A1* | 11/2015 | Cosman, Jr. | A61B 34/10 606/35 |
| 2016/0095500 A1* | 4/2016 | Kumagai | A61B 1/3137 600/109 |
| 2016/0120599 A1 | 5/2016 | Amirana et al. | |
| 2016/0249859 A1 | 9/2016 | Babkin et al. | |
| 2017/0014202 A1 | 1/2017 | Ransbury et al. | |
| 2017/0014600 A1* | 1/2017 | Mogul | A61M 25/0136 |
| 2017/0021143 A1 | 1/2017 | Barrish et al. | |
| 2017/0100197 A1 | 4/2017 | Zubiate et al. | |
| 2017/0203076 A1* | 7/2017 | Groneberg | A61M 25/0054 |
| 2017/0231474 A1 | 8/2017 | Saadat et al. | |
| 2017/0319233 A1 | 11/2017 | Fonger et al. | |
| 2018/0078737 A1 | 3/2018 | Gonzalez | |
| 2018/0289419 A1 | 10/2018 | Ladtkow et al. | |
| 2018/0304040 A1* | 10/2018 | Jalgaonkar | A61M 25/0054 |
| 2019/0133705 A1 | 5/2019 | Riojas et al. | |
| 2019/0343571 A1 | 11/2019 | Shadduck | |
| 2020/0163707 A1* | 5/2020 | Sliwa | A61B 18/082 |
| 2020/0179651 A1* | 6/2020 | Scheltes | A61M 25/0147 |
| 2020/0297415 A1* | 9/2020 | Marshik | A61B 90/361 |
| 2020/0337524 A1 | 10/2020 | Saeed et al. | |

FOREIGN PATENT DOCUMENTS

| | | |
|---|---|---|
| JP | 2016501696 A | 1/2016 |
| JP | 2017537681 A | 12/2017 |
| JP | 2018000757 A | 1/2018 |
| JP | 2019520956 A | 7/2019 |
| WO | 2015085307 A1 | 6/2015 |
| WO | 2017192897 A1 | 11/2017 |
| WO | WO2019094413 A1 | 5/2019 |

OTHER PUBLICATIONS

Extended European Search Report issued in EP07716358.2 on Apr. 24, 2014.

ISA, "International Search Report", PCT/US20/61070, Feb. 10, 2021.

ISA, "International Search Report", PCT/US20/61093, Feb. 9, 2021.

ISA, "International Search Report", PCT/US20/61100, Feb. 10, 2021.

ISA, "International Search Report", PCT/US20/61078, Mar. 25, 2021.

ISA, "International Search Report", PCT/US2018/059547, Jan. 24, 2019.

Notice of Reasons for Refusal of the Japanese Patent Office in related Japanese Patent Appl. No. 2022-528981, dated Jul. 16, 2024, 10 pages.

(56)          References Cited

OTHER PUBLICATIONS

First Examination Report of the IP Australia in related Australian
Appl. No. 2020386532, dated Mar. 27, 2025, 5 pages.
Office Action of the Korean Intellectual Property Office in related
Korean Appl. No. 2022-7019532, dated Jun. 10, 2025, 22 pages.

* cited by examiner

INSTRUMENT PORT FOR EPICARDIAL ABLATION WITH ANATOMICAL EPICARDIAL STRUCTURES AND REAL-TIME LESION IMAGE PROCESSOR

CROSS-REFERENCE TO RELATED APPLICATIONS

This application claims priority to U.S. Provisional Application No. 62/936,736, titled "Instrument Port for Epicardial Ablation," filed on Nov. 18, 2019 and to U.S. Provisional Application No. 63/076,075, titled "Instrument Port for Epicardial Ablation with Unidirectional Offset Balloon," filed on Sep. 9, 2020, which are hereby incorporated by reference.

STATEMENT REGARDING FEDERALLY-SPONSORED RESEARCH

This invention was made with government support under Grant No. R41HL147694, awarded by the National Heart, Lung, and Blood Institute of the National Institutes of Health. The government has certain rights in the invention.

TECHNICAL FIELD

This application relates generally to medical devices for treating cardiac conditions such as ventricular tachycardia.

BACKGROUND

Endocardial and/or epicardial ablation is/are currently used to treat ventricular tachycardia, a life-threatening heart rhythm disorder. To perform endocardial ablation, a doctor inserts an ablation catheter into the patient's heart through a vein or artery to ablate the regions of the heart that causes the arrhythmia. In contrast, epicardial ablation is performed from the outside of the heart.

During an epicardial ablation procedure, the doctor can visualize the ablation catheter and heart tissue using fluoroscopy and 3D electro-anatomical voltage mapping. However, these visualization methods have limitations. For example, it is difficult or impossible to identify coronary vessels, scar tissue, fat pads, and the phrenic nerve using these visualization methods, which can lead to undesired complications.

In addition, existing ablation catheters are inserted tangentially through the pericardium so that they lay flat against the heart's surface, as illustrated in FIG. 1. In this orientation, the ablation catheter 100 emits energy into the heart tissue 110 to create lesions 130 in the heart tissue 110 and the pericardium 120. It is undesirable to ablate the pericardium 120 because it may damage the phrenic nerve 140 located on the pericardium's external surface. In addition, this orientation provides the doctor with little control over the force applied by the ablation catheter 100, which may lead to unstable heart tissue contact.

It would be desirable to overcome these and/or other deficiencies in the art.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is direct to an instrument port comprising: an elongated shaft having proximal and distal ends and extending along a shaft axis, the elongated shaft having a fluid port defined in an external surface at the distal end of the elongated shaft; a bendable shaft having a proximal end attached to the distal end of the elongated shaft along a shaft axis, the bendable shaft configured to bend only within a pivot plane that is defined by the shaft axis and a pivot axis that is orthogonal to the shaft axis; a steerable tip attached to a distal end of the bendable shaft, the steerable tip including an imaging system that includes: a camera disposed at a distal end of the steerable tip; and a light emitter disposed at the distal end of the steerable tip. The instrument port also comprises an offset balloon attached to the external surface of the elongated shaft, the offset balloon having an internal volume in fluid communication with the fluid port, the offset balloon having an inflated state and a deflated state; a handle attached to the proximal end of the elongated shaft, the handle including a lever in mechanical communication with the bendable shaft to adjust a customizable angle of the steerable tip, the customizable angle measured between the shaft axis and the tip axis; a fluid tube disposed in the elongated shaft, the fluid tube fluidly coupled to the fluid port; a working tube disposed in the elongated shaft, the working tube forming a working channel; an ablation catheter disposed in the working channel, the ablation catheter configured to form a lesion at a surgical site; and a microprocessor-based controller in electrical communication with the imaging system, the controller configured to: acquire image data of the surgical site from the camera; automatically detect, in real time, the lesion formed at the surgical site; and automatically stop the ablation catheter when the lesion has a predetermined characteristic.

In one or more embodiments, the predetermined characteristic comprises a predetermined size. In one or more embodiments, the predetermined characteristic comprises a predetermined color. In one or more embodiments, the customizable angle is within a range of 0° to 90°, and when the bendable shaft is in an unbent state: the bendable shaft extends along the shaft axis, and the customizable angle is 0°.

In one or more embodiments, the offset balloon has an inflated state and a deflated state, and in the inflated state, the offset balloon has a height, measured with respect to a vertical that is orthogonal to the shaft axis, that is greater than a bend distance, measured from the distal end of the steerable tip to an external surface on the distal end of the elongated shaft, when the customizable angle is 90°. In one or more embodiments, the in the inflated state the offset balloon is radially asymmetrically inflated. In one or more embodiments, a first portion of the wall has a relatively thin wall thickness compared to a second portion of the wall that has a relatively thick wall thickness compared to the first portion of the wall, and the first portion of the wall is on a first side of the elongated shaft.

In one or more embodiments, an internal diameter of the working channel is greater than an external diameter of the ablation catheter, and a fluid channel is defined between the internal diameter of the working channel and the external diameter of the ablation catheter. In one or more embodiments, the fluid channel is fluidly coupled to a flush liquid source and/or to a vacuum source. In one or more embodiments, the ablation catheter comprises an RF ablation catheter.

In one or more embodiments, the working tube comprises a flexible cylinder. In one or more embodiments, the flexible cylinder comprises a wire-reinforced liner. In one or more embodiments, the wire-reinforced liner comprises a tube body comprising fluorinated ethylene propylene and a spiral wire. In one or more embodiments, an internal surface of the flexible cylinder comprises only the tube body to form a smooth surface to receive the medical instrument. In one or more embodiments, the shaft comprises a metal tube having an internal surface and an external surface, and a pattern of slits is defined in the shaft to increase a shaft flexibility.

In one or more embodiments, the metal tube comprises stainless steel. In one or more embodiments, the grooves are laser cut. In one or more embodiments, the pattern comprises an interrupted spiral. In one or more embodiments, the pattern comprises a plurality of fins that extend circumferentially on first and second sides of the metal tube, the fins on the first side and the fins on the second side are separated by first and second gaps, the first and second gaps extending along a plane defined by the shaft axis and an axis orthogonal to the shaft axis.

Another aspect of the invention is directed to a method for controlling an epicardial ablation procedure comprising: inserting an instrument port comprising an ablation tool, an optical camera and an optical light emitter into an epicardial cavity proximal to a target region; providing optical light into said epicardial cavity through said optical light emitter to illuminate said target region; obtaining a first image of said target region using said optical camera; steering a tip of said ablation tool towards said target region; applying an ablation energy to said target region using the ablation tool so as to form a lesion in or on said target region; obtaining a second image of said target region using said optical camera; and processing at least one of said first and second images in an image processor so as to determine a characteristic of said lesion.

In one or more embodiments, the method further comprises obtaining a third image of said target region after the step of obtaining the second image, and using at least two of said first, second and third images to determine a characteristic of said lesion. In one or more embodiments, said characteristic comprises a size of said lesion. In one or more embodiments, characteristic comprises a rate of growth of said lesion. In one or more embodiments, the method further comprises controlling an ablation application to said target region based on determining that a desired outcome has been achieved in said lesion.

In one or more embodiments, the characteristic of the lesion is determined in real time. In one or more embodiments, the method further comprises processing at least one of said first and second images in an image processor so as to automatically detect an anatomical feature in said target region.

Another aspect of the invention is directed to an instrument port comprising: an elongated shaft having proximal and distal ends and extending along a shaft axis, the elongated shaft having a fluid port defined in an external surface at the distal end of the elongated shaft; a steerable tip attached to the distal end of the shaft; an offset balloon attached to the external surface of the elongated shaft, the offset balloon having an internal volume in fluid communication with the fluid port, the offset balloon having an inflated state and a deflated state, wherein in the inflated state the offset balloon is radially asymmetrically inflated with respect to the shaft axis; and a working tube disposed in the elongated shaft, the working tube forming a working channel to receive a medical instrument.

In one or more embodiments, the instrument port further comprises a fluid tube disposed in the elongated shaft, the fluid tube fluidly coupled to the fluid port. In one or more embodiments, a proximal side of the offset balloon is attached to the external surface of the elongated shaft on a proximal side of the fluid port, and a distal side of the offset balloon is attached to the external surface of the elongated shaft on a distal side of the fluid port.

In one or more embodiments, the offset balloon is formed of a wall having a variable wall thickness. In one or more embodiments, a first portion of the wall has a relatively thin wall thickness compared to a second portion of the wall that has a relatively thick wall thickness compared to the first portion of the wall, and the first portion of the wall is on the first side of the elongated shaft, whereby in the inflated state the offset balloon is radially asymmetrically inflated. In one or more embodiments, the proximal and distal sides of the offset balloon are attached to the external surface by tie-downs, bonds, and/or heat seals.

In one or more embodiments, the offset balloon is attached to the external surface only on a first side of the elongated shaft, and an offset balloon aperture in the offset balloon is fluidly coupled to the fluid port. In one or more embodiments, the offset balloon is disposed between a balloon restriction tube section and the external surface on a second side of the elongated shaft, the balloon restriction tube section restricting an inflation volume of the offset balloon to only a first side of the elongated shaft when the offset balloon is in the inflated state. In one or more embodiments, the balloon restriction tube section comprises a horizontal cylindrical segment. In one or more embodiments, the offset balloon is radially asymmetrically inflated with respect to an inflation plane, the shaft axis lying in the inflation plane.

In one or more embodiments, the offset balloon has a partially-inflated state in which a partially-inflated volume of the offset balloon is in a range of about 10% to about 90% of a fully-inflated volume of the offset balloon, the offset balloon having the fully-inflated volume when the offset balloon is in the inflated state.

Another aspect of the invention is directed to an instrument port comprising: an elongated shaft having proximal and distal ends and extending along a shaft axis, the elongated shaft having a fluid port defined in an external surface at the distal end of the elongated shaft; a bendable shaft attached to the distal end of the elongated shaft; a steerable tip attached to the distal end of the shaft, the steerable tip extending along a tip axis; an offset balloon attached to the external surface of the elongated shaft, the offset balloon having an internal volume in fluid communication with the fluid port, the offset balloon having an inflated state and a deflated state, wherein in the inflated state the offset balloon is only inflated on a first side of the elongated shaft; a fluid tube disposed in the elongated shaft, the fluid tube fluidly coupled to the fluid port; and a working tube disposed in the elongated shaft, the working tube forming a working channel to receive a medical instrument.

In one or more embodiments, the instrument port further comprises a handle attached to the proximal end of the elongated shaft, the handle including a handle fluid port that is fluidly coupled to the fluid tube to introduce or receive a fluid. In one or more embodiments, a distal end of the fluid tube is capped to define a closed fluid path between the fluid port and the fluid port. In one or more embodiments, the fluid tube includes a fluid tube aperture, and the fluid tube is attached to an internal surface at the distal end of the elongated shaft to fluidly couple the fluid tube aperture and the fluid port.

In one or more embodiments, a proximal side of the offset balloon is attached to the external surface of the elongated shaft on a proximal side of the fluid port, and a distal side of the offset balloon is attached to the external surface of the elongated shaft on a distal side of the fluid port. In one or more embodiments, the offset balloon is formed of a wall having a variable wall thickness. In one or more embodiments, a first portion of the wall has a relatively thin wall thickness compared to a second portion of the wall that has a relatively thick wall thickness compared to the first portion of the wall, and the first portion of the wall is on the first side of the elongated shaft, whereby the offset balloon is radially asymmetrically inflated, with respect to the shaft axis, in the inflated state.

In one or more embodiments, the proximal and distal sides of the offset balloon are attached to the external surface by tie-downs, bonds, and/or heat seals. In one or more embodiments, the proximal and distal sides of the offset balloon are attached to the external surface on the first side of the elongated shaft, and an offset balloon aperture in the offset balloon is fluidly coupled to the fluid port.

In one or more embodiments, the offset balloon is disposed between a balloon restriction tube section and the external surface on a second side of the elongated shaft, the balloon restriction tube section restricting an inflation volume of the offset balloon to only the first side of the elongated shaft when the offset balloon is in the inflated state. In one or more embodiments, the balloon restriction tube section comprises a horizontal cylindrical segment. In one or more embodiments, the offset balloon is radially asymmetrically inflated with respect to an inflation plane, the shaft axis lying the inflation plane.

In one or more embodiments, the offset balloon has a partially-inflated state in which a partially-inflated volume of the offset balloon is in a range of about 10% to about 90% of a fully-inflated volume of the offset balloon, the offset balloon having the fully-inflated volume when the offset balloon is in the inflated state.

Yet another aspect of the invention is directed to an instrument port comprising: an elongated shaft having proximal and distal ends and extending along a shaft axis, the elongated shaft having a fluid port defined in an external surface at the distal end of the elongated shaft; a bendable shaft attached to the distal end of the elongated shaft; a steerable tip attached to the distal end of the shaft, the steerable tip extending along a tip axis; an offset balloon attached to the external surface of the elongated shaft, the offset balloon having an internal volume in fluid communication with the fluid port, the offset balloon having an inflated state and a deflated state; a fluid tube disposed in the elongated shaft, the fluid tube fluidly coupled to the fluid port; and a working tube disposed in the elongated shaft, the working tube forming a working channel to receive a medical instrument.

In one or more embodiments, the instrument port further comprises a handle attached to the proximal end of the elongated shaft, the handle including a handle fluid port that is fluidly coupled to the fluid tube to introduce or receive a fluid. In one or more embodiments, a distal end of the fluid tube is capped to define a closed fluid path between the fluid port and the fluid port. In one or more embodiments, the fluid tube includes a fluid tube aperture, and the fluid tube is attached to an internal surface at the distal end of the elongated shaft to fluidly couple the fluid tube aperture and the fluid port.

In one or more embodiments, a proximal side of the offset balloon is attached to the external surface of the elongated shaft on a proximal side of the fluid port, and a distal side of the offset balloon is attached to the external surface of the elongated shaft on a distal side of the fluid port. In one or more embodiments, in the inflated state the offset balloon is radially symmetrically inflated with respect to the shaft axis.

In one or more embodiments, the offset balloon has a partially-inflated state in which a partially-inflated volume of the offset balloon is in a range of about 10% to about 90% of a fully-inflated volume of the offset balloon, the offset balloon having the fully-inflated volume when the offset balloon is in the inflated state.

Another aspect of the invention is directed to an instrument port comprising: an elongated shaft having proximal and distal ends and extending along a shaft axis; a flexible shaft attached to the distal end of the elongated shaft, the flexible shaft configured to bend only within a pivot plane that is defined by the shaft axis and a pivot axis that is orthogonal to the shaft axis; a steerable tip attached to the distal end of the shaft, the steerable tip extending along a tip axis; a handle attached to the proximal end of the elongated shaft, the handle including a lever in mechanical communication with the flexible shaft to adjust a customizable angle of the steerable tip, the customizable angle measured between the shaft axis and the tip axis; and a working tube disposed in the elongated shaft and flexible shaft, the working tube forming a working channel to receive a medical instrument.

In one or more embodiments, in an unbent state: the flexible shaft extends along the shaft axis, and the flexible shaft includes: a plurality of mechanical rings concentrically disposed along the shaft axis, the plurality of mechanical rings including neighboring mechanical ring pairs, and each neighboring mechanical ring pair is mechanically coupled by a pair of mechanical links, wherein a respective third axis passes through each pair of mechanical links, the respective third axis orthogonal to the shaft and pivot axes. In one or more embodiments, the pairs of mechanical links mechanically restrict a bending direction of the flexible shaft to the pivot plane.

In one or more embodiments, the lever is mechanically coupled to a wire that extends to a distal end of the flexible shaft, the wire attached to an internal surface of the flexible shaft, the pivot axis passing through the internal surface. In one or more embodiments, the lever is mechanically coupled to a wire rope that extends to the distal end of the flexible shaft, the wire rope comprising the wire.

In one or more embodiments, the lever is mechanically coupled to a spindle disposed in the handle. In one or more embodiments, the wire is attached to the spindle, and pulling the lever causes the spindle to rotate to pull the wire towards the proximal end of the elongated shaft to thereby cause the flexible shaft to bend in a first direction. In one or more embodiments, the handle includes a mechanical lock that applies a force against the spindle to set the customizable angle of the flexible shaft.

In one or more embodiments, the customizable angle is within a range of 0° to 90°, and when the flexible shaft is in an unbent state: the flexible shaft extends along the shaft axis, and the customizable angle is 0°. In one or more embodiments, the instrument port further comprises an offset balloon attached to the distal end of the elongated shaft.

In one or more embodiments, the elongated shaft is flexible, the elongated shaft has a flexed state and an unflexed state, and in the unflexed state, the elongated shaft extends along the shaft axis. In one or more embodiments, when the customizable angle is adjusted, the elongated shaft stays in the unflexed state. In one or more embodiments, when the customizable angle is adjusted, the elongated shaft stays in the flexed state, the elongated shaft having a same flexed position while the customizable angle is adjusted.

Another aspect of the invention is directed to an instrument port comprising: an elongated shaft having proximal and distal ends and extending along a shaft axis; a flexible shaft attached to the distal end of the elongated shaft, the flexible shaft configured to bend only within a pivot plane that is defined by the shaft axis and a pivot axis that is orthogonal to the shaft axis; a steerable tip attached to the distal end of the shaft, the steerable tip extending along a tip axis; a handle attached to the proximal end of the elongated shaft, the handle including: a first lever mechanically coupled to a first wire having an end attached to a first side of the flexible shaft, the first lever configured to pull the first wire to deflect the flexible shaft in a first direction within the pivot plane; and a second lever mechanically coupled to a second wire having an end attached to a second side of the flexible shaft, the second lever configured to pull the second wire to deflect the flexible shaft in a second direction that is opposite to the first direction, the second direction within the pivot plane; and a working tube disposed in the elongated shaft and flexible shaft, the working tube forming a working channel to receive a medical instrument.

In one or more embodiments, in an unbent state: the flexible shaft extends along the shaft axis, and the flexible shaft includes: a plurality of mechanical rings concentrically disposed along the shaft axis, the plurality of mechanical rings including neighboring mechanical ring pairs, and each neighboring mechanical ring pair is mechanically coupled by a pair of mechanical links, wherein a respective third axis passes through each pair of mechanical links, the respective third axis orthogonal to the shaft and pivot axes. In one or more embodiments, the pairs of mechanical links mechanically restrict a bending direction of the flexible shaft to the pivot plane.

In one or more embodiments, the first and second sides of the flexible shaft comprise internal surfaces disposed at a distal end of the flexible shaft, and the pivot axis passes through the internal surfaces of the first and second sides. In one or more embodiments, the first and second levers are mechanically coupled to first and second wire ropes, respectively, and the first and second wire ropes comprise the first and second wires, respectively.

In one or more embodiments, the first and second levers are mechanically coupled to a spindle disposed in the handle. In one or more embodiments, the first and second wires are attached to the spindle, and the spindle is configured to rotate in a first direction to pull the end of the first wire towards the proximal end of the elongated shaft when the first lever is pulled, thereby causing the flexible shaft to bend in the first direction, and the spindle is configured to rotate in a second direction to pull the end of the second wire towards the proximal end of the elongated shaft when the second lever is pulled, thereby causing the flexible shaft to bend in the second direction. In one or more embodiments, the spindle is configured to release a first force on the first wire when the spindle is rotated in the second direction, and the spindle is configured to release a second force on the second wire when the spindle is rotated in the first direction.

In one or more embodiments, the handle includes a mechanical lock that applies a force against the spindle to set the customizable angle of the flexible shaft. In one or more embodiments, the customizable angle is within a range of −90° to 90°, and when the flexible shaft is in an unbent state: the flexible shaft extends along the shaft axis, and the customizable angle is 0°. In one or more embodiments, the customizable angle is adjustable while a flexed position and a flexed orientation of the elongated shaft is maintained.

Another aspect of the invention is directed to an instrument port comprising: an elongated shaft having proximal and distal ends and extending along a shaft axis, the elongated shaft having a fluid port defined in an external surface at the distal end of the elongated shaft; a bendable shaft having a proximal end attached to the distal end of the elongated shaft along a shaft axis, the bendable shaft configured to bend only within a pivot plane that is defined by the shaft axis and a pivot axis that is orthogonal to the shaft axis; a steerable tip attached to a distal end of the bendable shaft, the steerable tip including: a camera disposed at a distal end of the steerable tip; and a light emitter disposed at the distal end of the steerable tip. The instrument port further comprises an offset balloon attached to the external surface of the elongated shaft, the offset balloon having an internal volume in fluid communication with the fluid port, the offset balloon having an inflated state and a deflated state; a handle attached to the proximal end of the elongated shaft, the handle including at least one lever in mechanical communication with the bendable shaft to adjust a customizable angle of the steerable tip, the customizable angle measured between the shaft axis and the tip axis; a fluid tube disposed in the elongated shaft, the fluid tube fluidly coupled to the fluid port; and a working tube disposed in the elongated shaft, the working tube forming a working channel to receive a medical instrument.

In one or more embodiments, the customizable angle is within a range of −90° to 90°, and when the bendable shaft is in an unbent state: the bendable shaft extends along the shaft axis, and the customizable angle is 0°. In one or more embodiments, the offset balloon has an inflated state and a deflated state, and in the inflated state, the offset balloon has a height, measured with respect to a vertical axis that is orthogonal to the shaft axis, that is greater than a bend distance, measured from the distal end of the steerable tip to an external surface on the distal end of the elongated shaft, when the customizable angle is 90°. In one or more embodiments, in the inflated state the offset balloon is radially asymmetrically inflated. In one or more embodiments, a first portion of the wall has a relatively thin wall thickness compared to a second portion of the wall that has a relatively thick wall thickness compared to the first portion of the wall, and the first portion of the wall is on a first side of the elongated shaft.

In one or more embodiments, the instrument port further comprises an RF ablation catheter, wherein: an internal diameter of the working channel is greater than an external diameter of RF ablation catheter, and a fluid channel is defined between the internal diameter of the working channel is greater than an external diameter of RF ablation catheter. In one or more embodiments, the fluid channel is fluidly coupled to a flush liquid source and/or to a vacuum source.

In one or more embodiments, the working tube comprises a flexible cylinder. In one or more embodiments, the flexible cylinder comprises a wire-reinforced liner. In one or more embodiments, the wire-reinforced liner comprises a tube body comprising fluorinated ethylene propylene and a spiral wire. In one or more embodiments, an internal surface of the flexible cylinder comprises only the tube body to form a smooth surface to receive the medical instrument.

In one or more embodiments, the elongated shaft comprises a metal tube, and a pattern of slits is defined in the shaft to increase a shaft flexibility. In one or more embodiments, the metal tube comprises stainless steel. In one or more embodiments, the grooves are laser cut. In one or more embodiments, the pattern comprises an interrupted spiral. In one or more embodiments, the pattern comprises a plurality of fins that extend circumferentially on first and second sides of the metal tube, and the fins on the first side and the fins on the second side are separated by first and second gaps, the first and second gaps extending along a plane defined by the shaft axis and an axis orthogonal to the shaft axis.

In one or more embodiments, the offset balloon has a partially-inflated state in which a partially-inflated volume of the offset balloon is in a range of about 10% to about 90% of a fully-inflated volume of the offset balloon, the offset balloon having the fully-inflated volume when the offset balloon is in a fully-inflated state.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

An instrument port includes a handle, an elongated shaft, a bendable shaft, and a steerable tip. The bendable shaft can be controllably bent in one plane using one or more levers on the handle. A proximal end of the bendable shaft is mechanically coupled to the elongated shaft, and a distal end of the bendable shaft is mechanically coupled to the steerable tip. When the bendable shaft is in an unbent state, the bendable shaft extends along a shaft axis along which the elongated shaft extends. When the bendable shaft is in a bent state, the bendable shaft bends or flexes with respect to the shaft axis to direct the steerable tip to a customizable angle or orientation with respect to the shaft axis. The bendable shaft can bend without affecting the position, shape, orientation, and/or behavior of the elongated shaft. For example, the elongated shaft can remain in a flexed state while the bendable shaft 220 transitions from the unbent state to the bent state. Alternatively, the elongated shaft can remain in an unflexed state while the bendable shaft 220 transitions from the unbent state to the bent state The customizable angle can improve the field-of-view of an anatomical region during a medical procedure using an imaging system disposed on the steerable tip. In addition, the customizable angle can set the angle at which a medical instrument, such as an ablation catheter, exits the steerable tip which is advantageous.

An offset balloon is attached to the distal end of the elongated shaft. The offset balloon can be transitioned from a deflated state to an inflated state during the medical procedure. In the inflated state, the offset balloon can be disposed against an anatomical feature (e.g., heart tissue) to provide space between the elongated shaft and the anatomical feature. This space can be used to transition the bendable shaft from the unbent state to the bent state. The offset balloon can be symmetrically or asymmetrically inflated. In addition, the offset balloon can be partially inflated for example to customize the space between the elongated shaft and the anatomical feature.

A working channel extends through the instrument port from its proximal to distal ends. The working channel can be configured to have an internal radius that is greater than an external radius of the medical instrument to form a flush/vacuum channel therebetween. The flush/vacuum channel can be fluidly coupled to a flush liquid and/or vacuum source, which can be used to flush the external surface of the medical instrument before the medical procedure, to clean the face of the device to provide a clear image through the camera, to flush the surgical site during the medical procedure, and/or to apply a vacuum as needed to remove liquid and/or bodily fluids such as blood.

The instrument port can have various features as described in the accompany figures. These features can be combined and/or removed in various embodiments.

Figure 2:
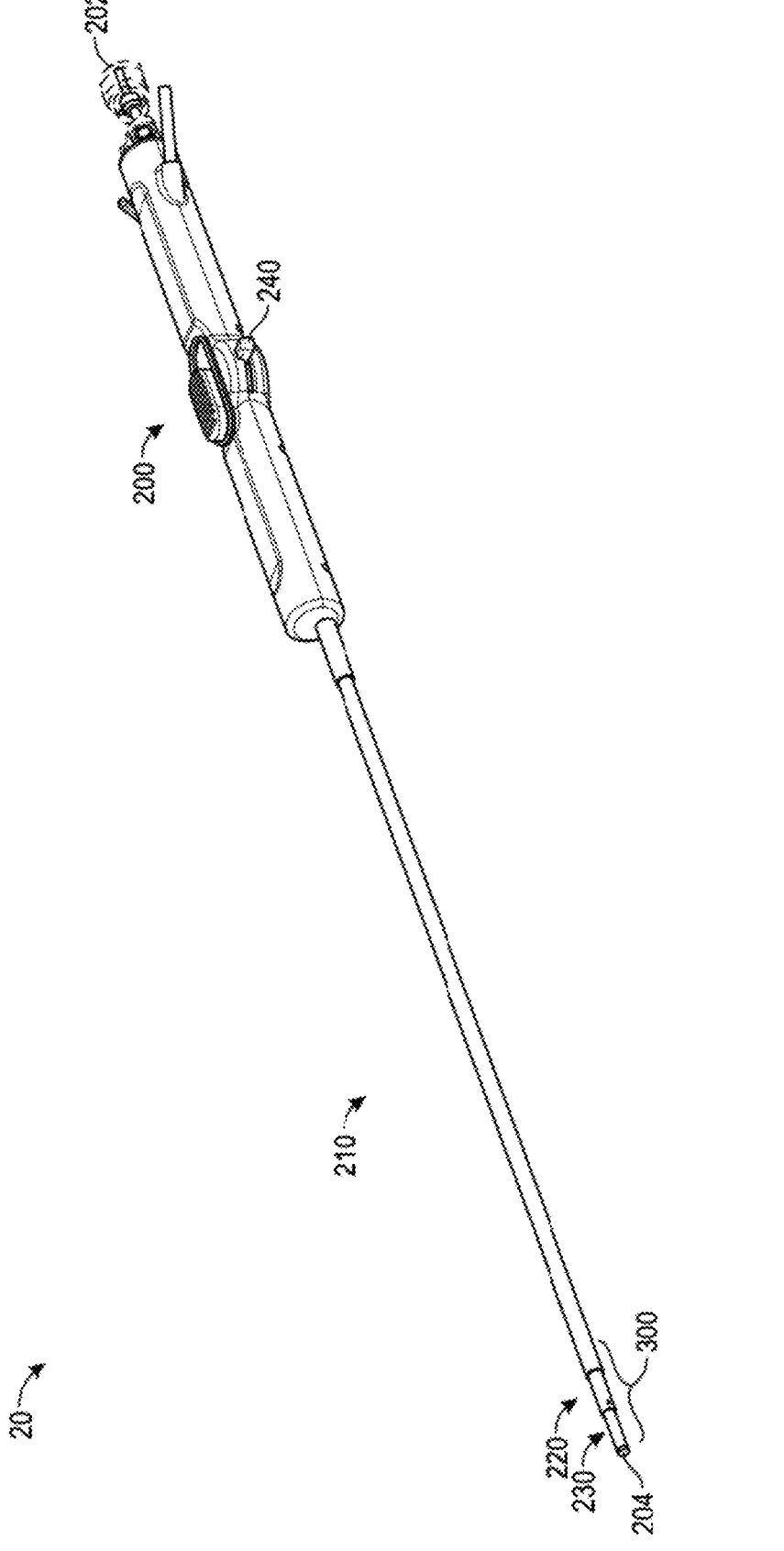
FIG. 2 is a perspective view of an instrument port according to an embodiment

FIG. 2 is a perspective view of an instrument port 20 according to an embodiment. The instrument port 20 includes a handle 200, an elongated shaft 210, a bendable shaft 220, and a steerable tip 230. The handle 200 is on a proximal end 202 of the instrument port 20. The steerable tip 230 is on a distal end 204 of the instrument port 20.

The bendable shaft 220 can be bent in response to the position of one or more levers 240 on the handle 200. The bendable shaft 220 can be configured to bend only in one plane (e.g., upwards or downwards) and to not bend in an orthogonal plane (e.g., side-to-side). The position and/or orientation of the steerable tip 230 can be controlled by activating the lever(s) 240 on the handle 200 which can set a customizable angle of the steerable tip 230 with respect to the elongated shaft 210 by bending the bendable shaft 220. In some embodiments, the bendable shaft 220 is optional. The bendable shaft 220 can bend without affecting the position, shape, orientation, and/or behavior of the elongated shaft 210.

Figure 3:
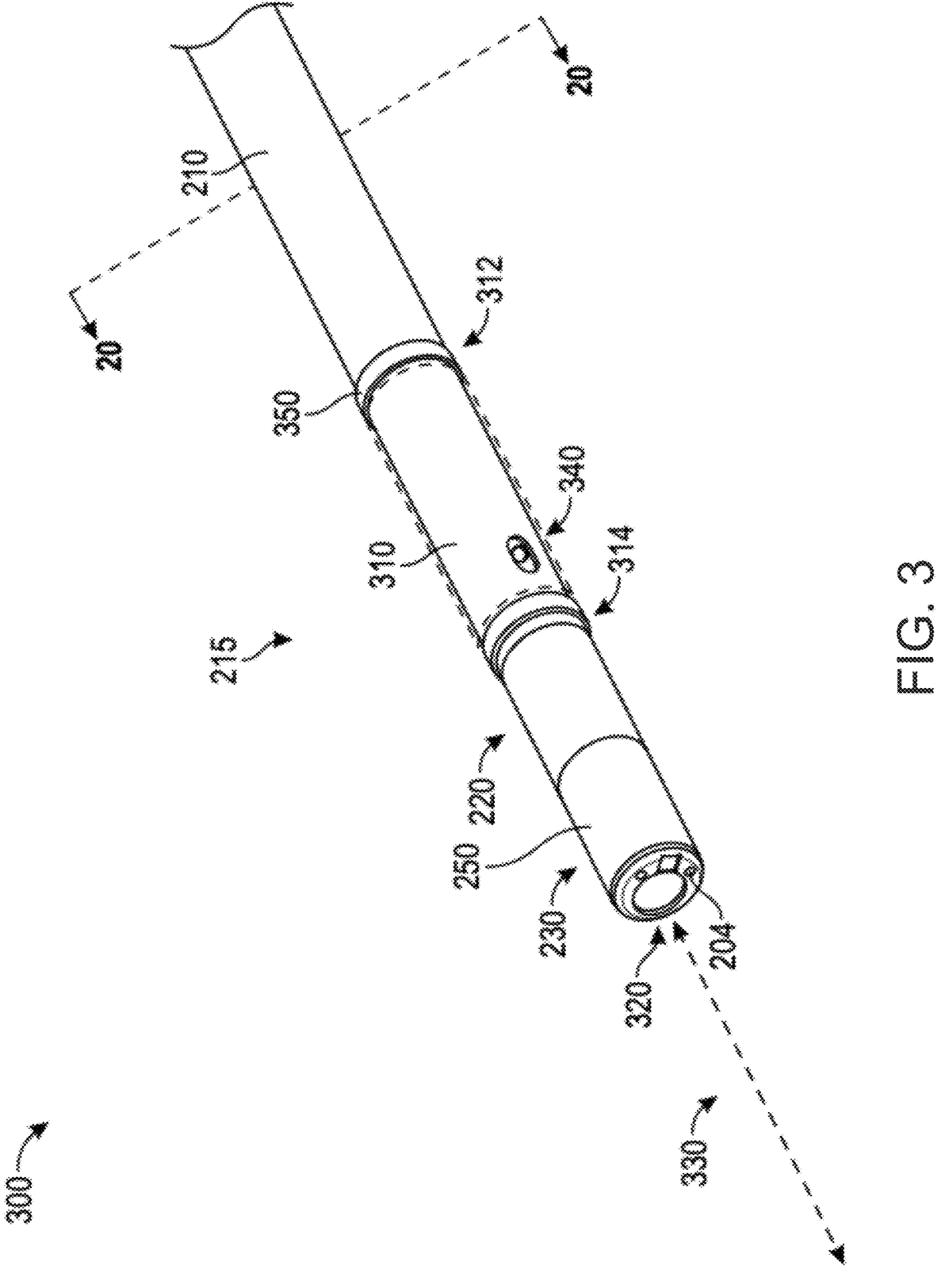
FIG. 3 is a perspective view of a distal portion of the instrument port according to an embodiment.

FIG. 3 is a perspective view of a distal portion 300 of the instrument port 20 according to an embodiment. In addition to the bendable shaft 220 and steerable tip 230, the distal portion 300 also includes an offset balloon 310, which is in a deflated state in FIG. 3. The offset balloon is located at a distal end or distal portion 215 of the elongated shaft 210. During a medical procedure, the offset balloon 310 can be inflated to create space between an anatomical feature and the instrument port 20. The space created by the offset balloon 310 in the inflated state can be used to bend the bendable shaft 220 to create a customizable angle of the steerable tip 230 during the medical procedure, for example to customize the angle at which a medical instrument (e.g., an ablation catheter such as ablation catheter 100) passes through a working channel 320 at the distal end 204 of the instrument port 20. When the inflated offset balloon 310 is disposed against an anatomical feature, the offset balloon 310 can provide stability to the instrument port 20 during the medical procedure.

The offset balloon 310 can be inflated with a fluid (e.g., gas and/or liquid). In one example, the offset balloon 310 is inflated with air. In another embodiment, the offset balloon 310 is inflated with saline or semi-saline water. The liquid can include a contrast agent that can be used to view the offset balloon 310 during the medical procedure such as with medical imaging (e.g., ultrasound, MRI, or another medical imaging technology). The internal volume of the offset balloon 310 is fluidly coupled to a fluid port 340 defined at or near the distal end 215 of the elongated shaft. The fluid port 340 can be used to introduce and remove fluid to/from the offset balloon 310 to inflate and deflate the offset balloon 310, respectively.

Figure 1:
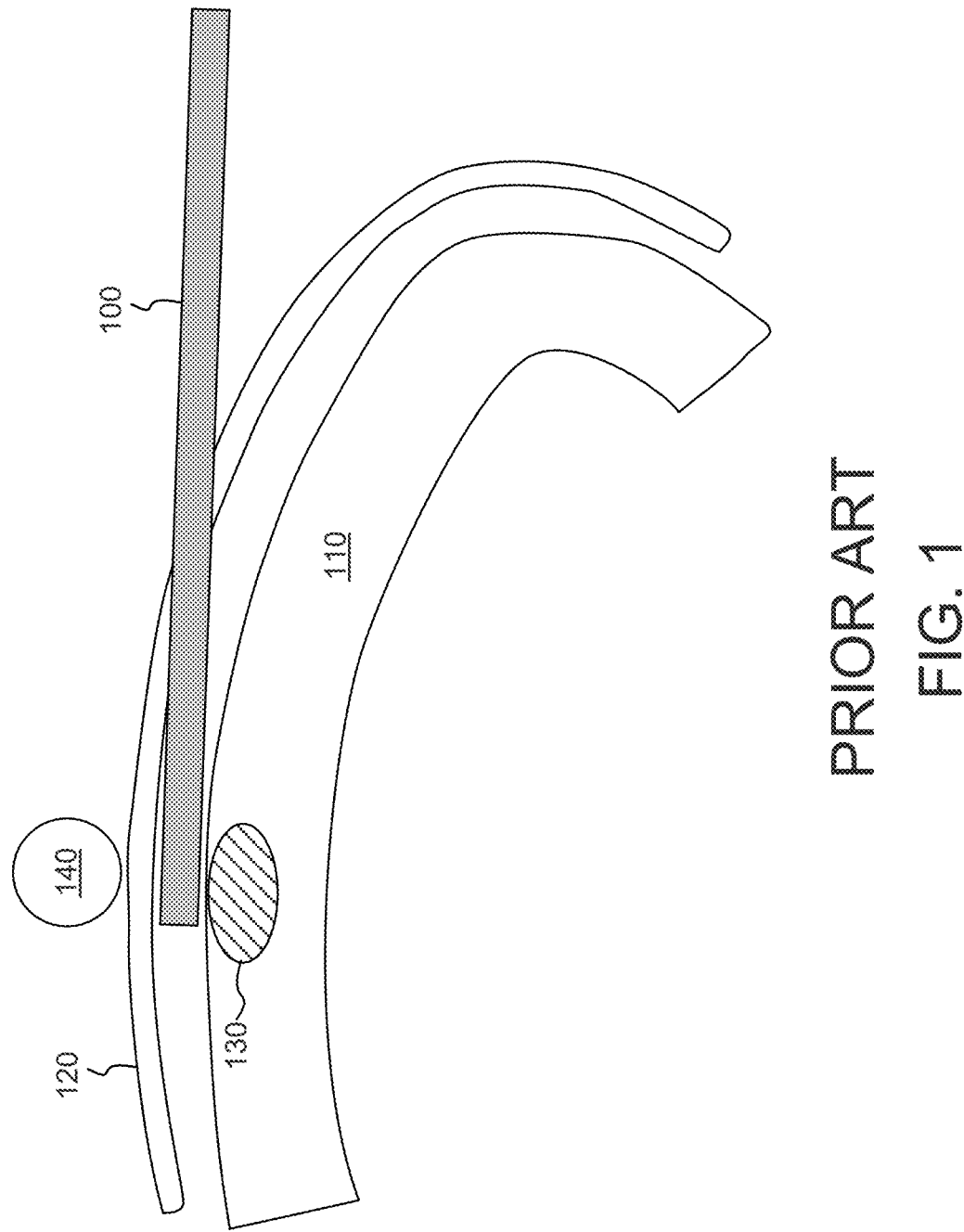
FIG. 1 is a block diagram of a medical procedure using an ablation catheter according to the prior art.

In the inflated state, the offset balloon 310 can be configured to be radially symmetrical or asymmetrical with respect to a shaft axis 330 that passes through the center of the elongated shaft 210, the bendable shaft 220 and the steerable tip 230 when the bendable shaft 220 is in an unbent state (e.g., as illustrated in FIGS. 1-3). The shaft axis 330 can be an axis of symmetry of the elongated shaft 210, the bendable shaft 220 and the steerable tip 230 when the bendable shaft 220 is in the unbent state.

The offset balloon 310 is attached to the distal end 215 of the elongated shaft 210 to create a fluid-tight seal around the fluid port 340. The proximal and distal ends 312, 314 of the offset balloon 310 are attached, at respective proximal and distal sides of the fluid port 340, using tie downs 350 in FIG. 3. In another embodiment, the offset balloon 310 can be attached by bonding the ends 312 of the offset balloon 310 to the elongated shaft 210, for example using an adhesive. In another embodiment, the offset balloon 310 can be attached by heat-sealing the walls of the offset balloon 310 to the elongated shaft 210. These and/or other attachment means can be used in other embodiments.

A sleeve 250 is disposed on at least the bendable shaft 220 and the steerable tip 230. The sleeve 250 can provide a smooth surface for insertion into the patient during a medical procedure to reduce the likelihood of tissue damage. The sleeve 250 can be flexible to conform to the bendable shaft 220 and the steerable tip 230 as their relative orientations and/or angles are adjusted during the medical procedure. The sleeve 250 can comprise and/or can consist of a polyolefin, a fluoropolymer, a polyether block amide (e.g., PEBAX® available from Arkema), and/or another material.

Figure 4:
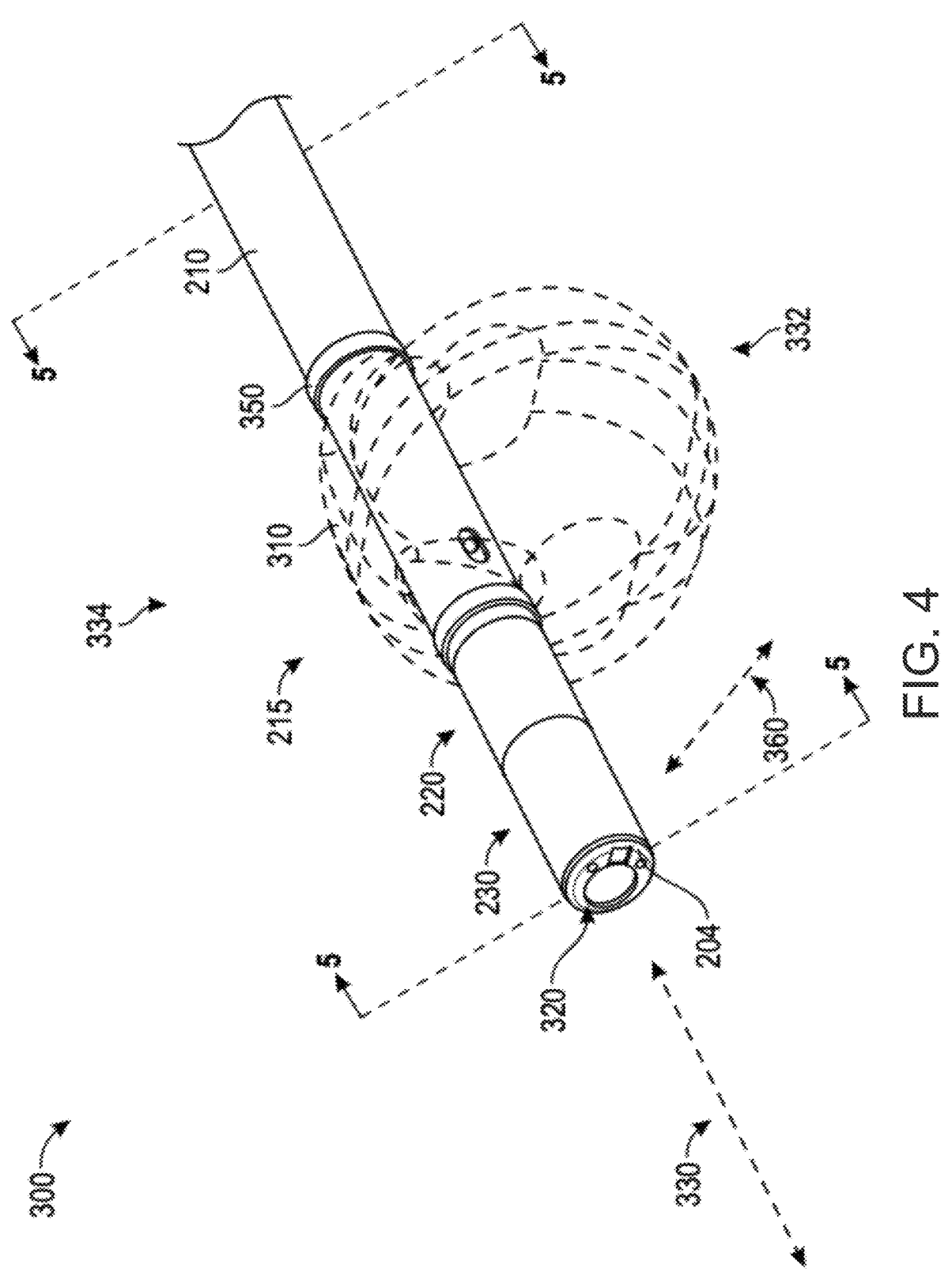
FIG. 4 is a perspective view of the distal portion of the instrument port when the offset balloon is radially asymmetrically inflated according to an embodiment.

FIG. 4 is a perspective view of the distal portion 300 of the instrument port 20 when the offset balloon 310 is radially asymmetrically inflated according to an embodiment. In this embodiment, the offset balloon 310 is inflated more on a first side 332 of the shaft axis 330 than on a second side 334 of the shaft axis 330. In an embodiment, the offset balloon 310 can have a variable wall thickness. In another embodiment, a portion of a semi-rigid tube can offset balloon 310 can be disposed on the second side 334 of the shaft axis 330 so that the offset balloon 310 inflates on the first side 332 of the shaft axis 330 and does not inflate on the second side 334 of the shaft axis.

In some embodiments, the offset balloon 310 can be partially inflated. For example, the offset balloon 310 can have a partially-inflated volume that is a percentage of the fully-inflated volume. In a specific example, the offset balloon 310 can have a partially-inflated state in which a partially-inflated volume of the offset balloon 310 is in a range of about 10% to about 90% of the fully-inflated volume, including about 20%, about 30%, about 40%, about 50%, about 60%, about 70%, and about 80%, or any percentage or percentage between any two of the foregoing percentages. The offset balloon 310 has the fully-inflated volume when the offset balloon 310 is in the inflated state (e.g., a fully-inflated state).

Figure 5:
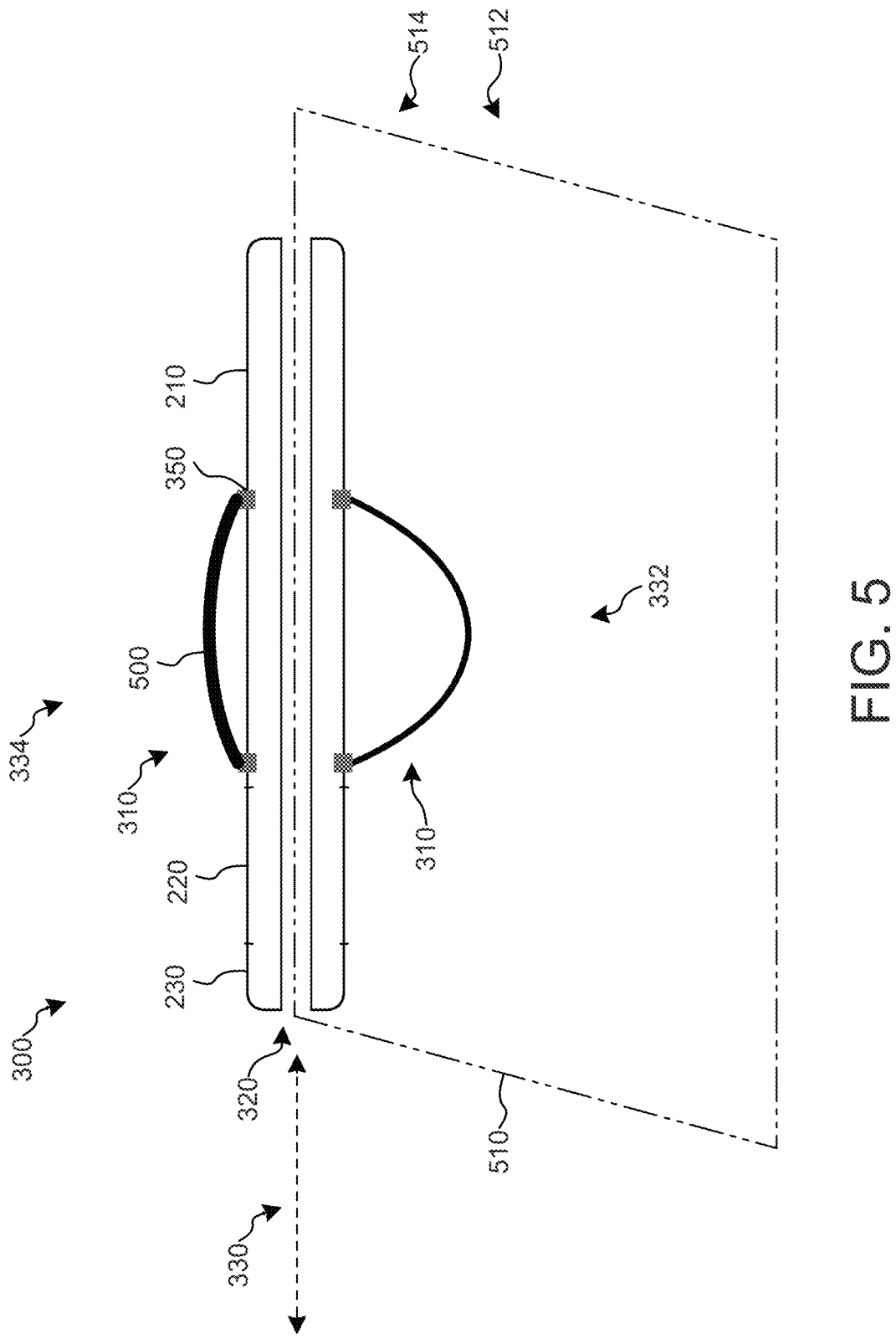
FIG. 5 is a cross-sectional view of the distal portion of the instrument port when the offset balloon is radially asymmetrically inflated according to an embodiment.

FIG. 5 is a cross-sectional view of the distal portion 300 of the instrument port 20 when the offset balloon 310 is radially asymmetrically inflated according to an embodiment. The cross-section view is taken through plane 5-5 in FIG. 4. This embodiment illustrates that offset balloon 310 is formed of a wall 500 having a variable cross-sectional thickness. The wall 500 on the first side 332 of the shaft axis 330 has a thinner cross-sectional thickness compared to the cross-sectional thickness of the wall 500 on the second side 334 of the shaft axis 330. Likewise, the wall 500 on the second side 334 of the shaft axis 330 has a thicker cross-sectional thickness compared to the cross-sectional thickness of the wall 500 on the first side 332 of the shaft axis 330. Since the relatively thick cross-sectional thickness of the wall 500 on the second side 334 of the shaft axis 330 requires more force to inflate and the relatively thin cross-sectional thickness of the wall 500 on the first side 332 of the shaft axis 330 requires less force to inflate, the offset balloon 310 is inflated more on the first side 332 of the shaft axis 330 than on the second side 332 of the shaft axis 330. For example, when the offset balloon 310 is inflated, about 60% to about 90% of the inflation volume in offset balloon 310 can be on the first side 332 of the shaft axis 330 while only about 10% to about 40% of the of the inflation volume offset balloon 310 can be on the second side 332 of the shaft axis 330.

The variable cross-sectional thickness of the wall 500 can also be measured with respect to an inflation plane 510. The inflation plane 510 passes through middle of the elongated shaft 210, the bendable shaft 220 and the steerable tip 230, along the shaft axis 330, when the bendable shaft 220 is in the unbent state. Thus, the shaft axis 330 lies in the inflation plane 510. In an embodiment, the inflation plane 510 can be described or defined by the shaft axis 330, which runs along the length of the instrument port 20, and a width axis 360 (FIG. 4), which run along the width of the instrument port. The width axis 360 is orthogonal to the shaft axis 330. Below 512 (e.g., on a first side of) the inflation plane 510, the offset balloon wall 500 has a thinner cross-sectional thickness compared to the cross-sectional thickness of the wall 500 above 514 (e.g., on a second side of) the inflation plane 510. Likewise, above 514 (e.g., on a second side of) the inflation plane 510, the offset balloon wall 500 has a thicker cross-sectional thickness compared to the cross-sectional thickness of the wall 500 below 512 (e.g., on a first side of) the inflation plane 510. When the offset balloon 310 is inflated, about 60% to about 90% of the inflation volume in offset balloon 310 can be below 512 (e.g., on a first side of) the inflation plane 510 while only about 10% to about 40% of the of the inflation volume offset balloon 310 can be above 514 (e.g., on a second side of) the inflation plane 510.

Figure 6:
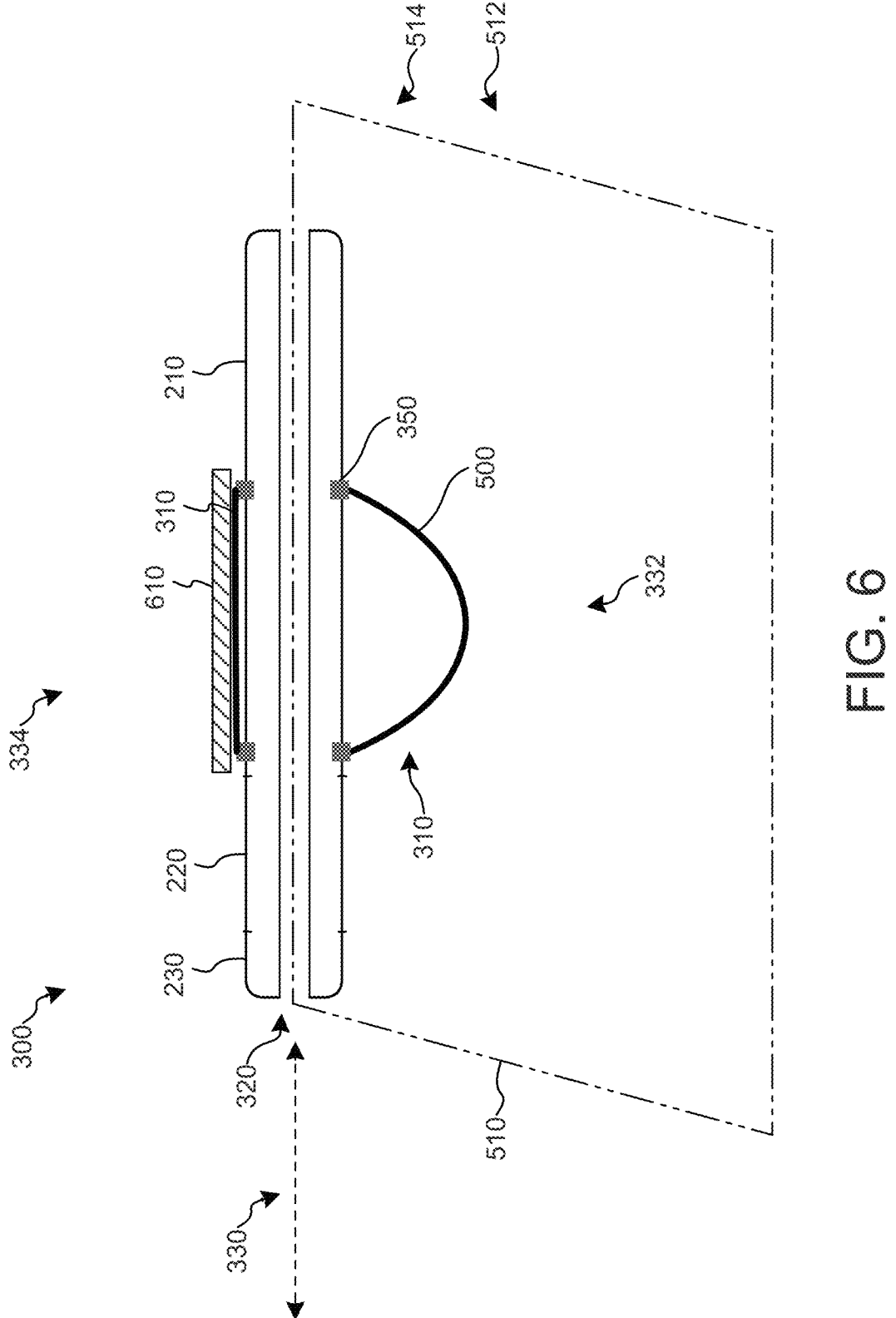
FIG. 6 is a cross-sectional view of the distal portion of the instrument port when the offset balloon is radially asymmetrically inflated according to an alternative embodiment.

FIG. 6 is a cross-sectional view of the distal portion 300 of the instrument port 20 when the offset balloon 310 is radially asymmetrically inflated according to an alternative embodiment. The cross section is taken through line through plane 5-5 in FIG. 4. In this embodiment, the wall 500 of the offset balloon 310 has a uniform cross-sectional thickness. A portion of a balloon restriction tube 610 (e.g., a tube cut along its length such as a horizontal cylindrical segment) is attached to the elongated shaft 210 over or on a portion of the offset balloon 310. The balloon restriction tube 610 is rigid and limits or restricts the inflation of the offset balloon 310 so that the offset balloon 310 only inflates where the balloon restriction tube 610 is not located. The balloon restriction tube 610 can be disposed over or on the offset balloon 310 above 514 (e.g., on a second side of) the inflation plane 510 so that the offset balloon 310 only inflates below 512 (e.g., on a first side of) the inflation plane 510. The balloon restriction tube 610 can comprise plastic, metal, and/or another material. The offset balloon 310 is inflated more on a first side 332 of the shaft axis 330 than on a second side 334 of the shaft axis 330.

Figure 7:
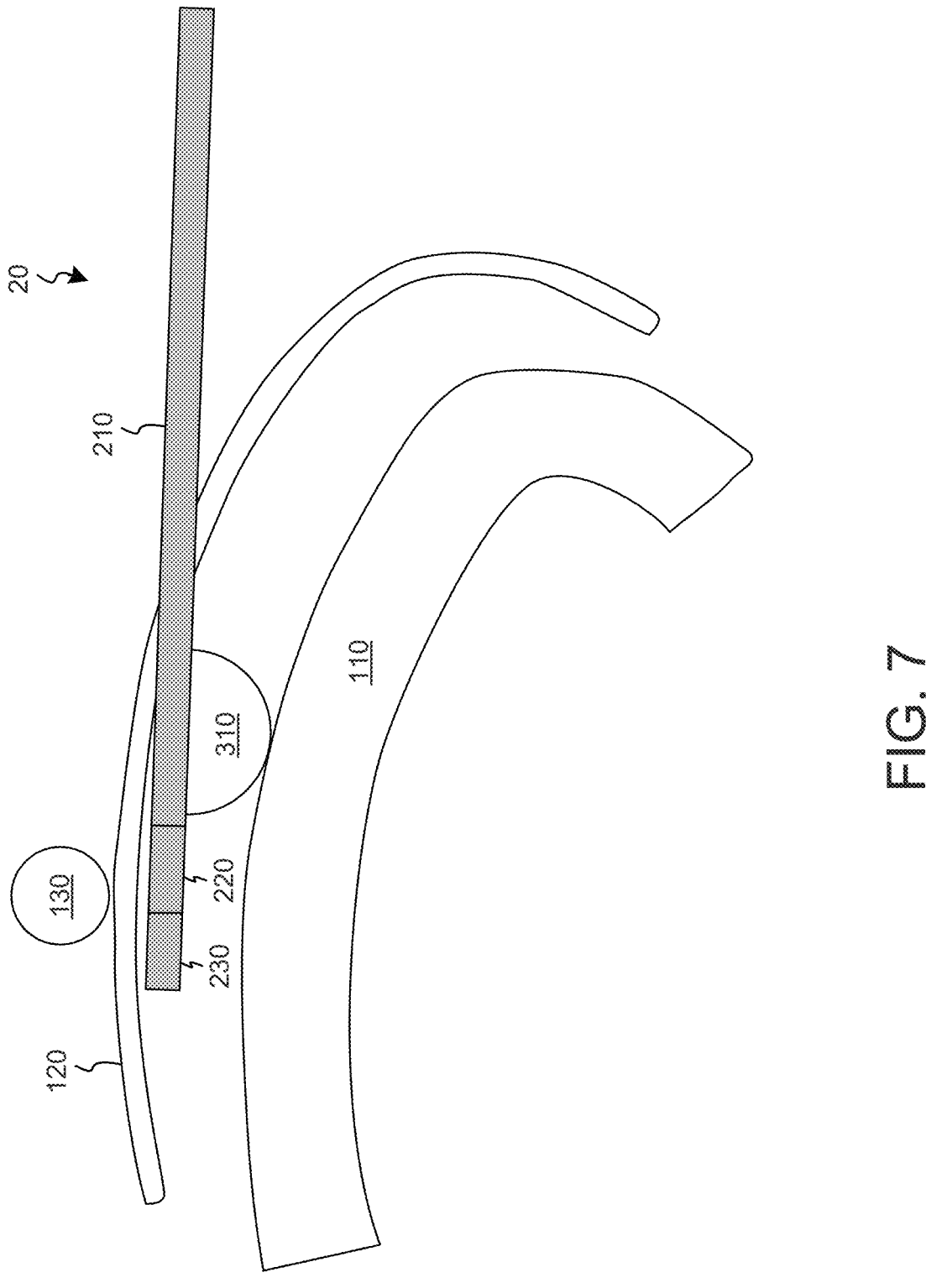
FIG. 7 illustrates a side view of the instrument port, when the offset balloon is radially asymmetrically inflated, during a medical procedure according to an embodiment.
Figure 8:
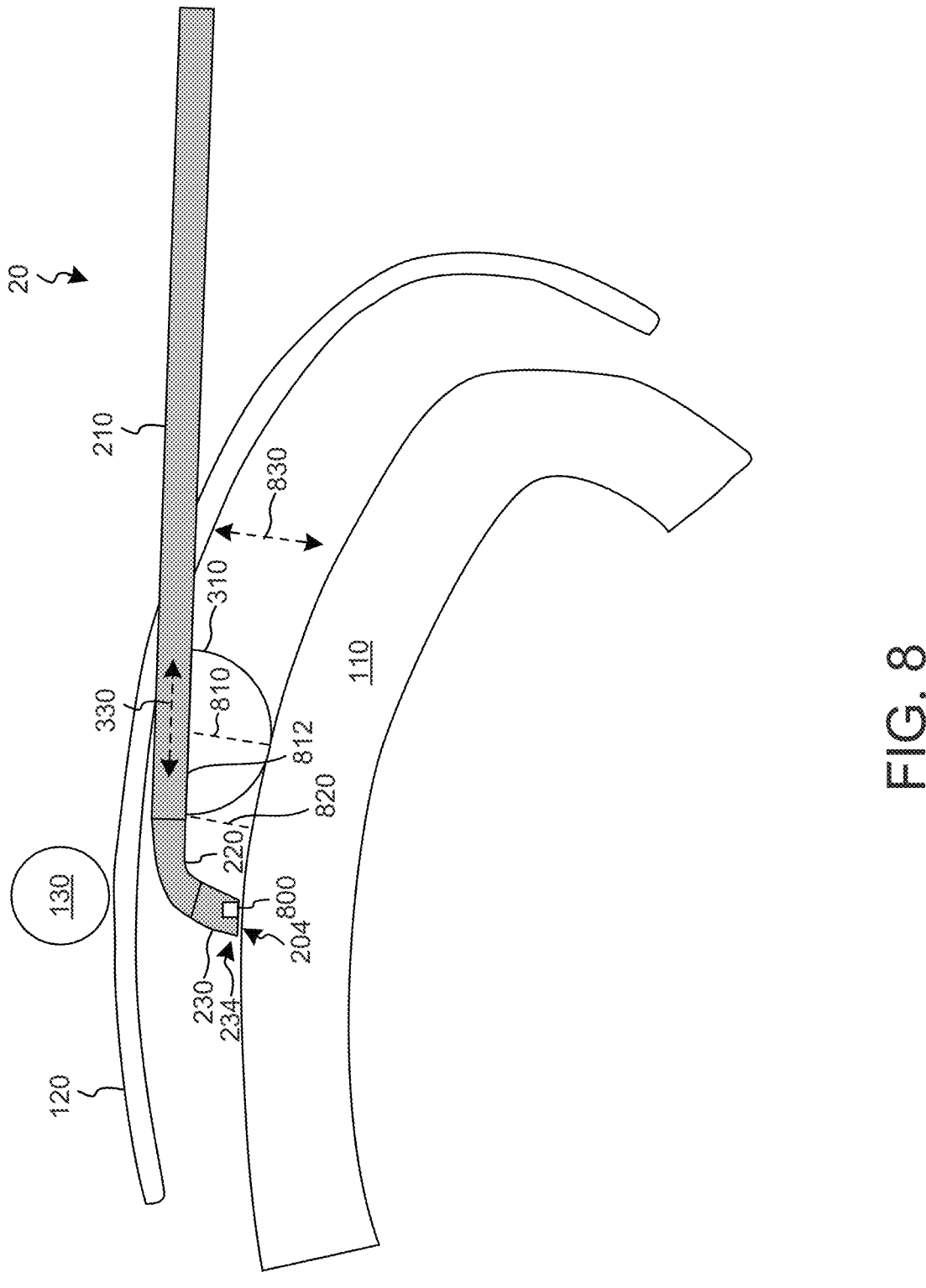
FIG. 8 illustrates a side view of the instrument port, when the offset balloon is radially asymmetrically inflated and the bendable shaft is in a bent state, during a medical procedure according to an embodiment.

FIG. 7 illustrates a side view of the instrument port 20 when the offset balloon 310 is radially asymmetrically inflated during a medical procedure according to an embodiment. Inflating the offset balloon 310 increases the distance between the heat tissue 110 and the instrument port 20 (e.g., the elongated shaft 210, bendable shaft 220, and steerable tip 230). One technical advantage is the increased distance between the heat tissue 110 and the instrument port 20, when the offset balloon 310 is inflated, provides the space necessary to bend the bendable shaft 220 towards the heart tissue 110, for example as illustrated in FIG. 8, to customize the position and angle of the steerable tip 230 with respect to the elongated shaft 210. For example the offset balloon 310 can have a radius or height 810 that is greater than or equal to a bend distance 820 between the distal end 204 of the steerable tip 230 and the external surface 812 of the distal end of the elongated shaft 210 when the bendable shaft 220 is in the bent state (e.g., when the customized angle between the steerable tip 230 and the elongated shaft 210 is 90°). The radius/height 810 and the bend distance 820 can be measured with respect to a vertical axis 830 that is orthogonal to the shaft axis 330. This provides sufficient space between for the bendable tip 220 to bend to adjust the customizable position and angle of the steerable tip 210.

The customizable position and angle of the steerable tip 230 can facilitate improved imaging the heart tissue 110 using an imaging system 800 located at the distal end 234 of the steerable tip 230. In addition, the customizable position and angle of the steerable tip 230 can allow an ablation catheter, inserted through the instrument port 20, to create a deeper lesion in the heart tissue 110 (e.g., compared to catheter 100) while protecting the phrenic nerve 140 from any damage. Further, the offset balloon 310 can provide a more precise and/or stable contact between the distal end 234 of the steerable tip 230 and the heart tissue 110 which can allow for the contact force needed to perform the ablation with the ablation catheter inserted through the instrument port 20. The ablation catheter can operate using any ablation technology including radiofrequency (RF), cryoablation, needle ablation, laser ablation, and/or electroporation.

FIGS. 7 and 8 also illustrate that the bendable shaft 220 can bend without affecting the position, shape, orientation, and/or behavior of the elongated shaft 210. For example, FIGS. 7 and 8 illustrate that the elongated shaft 210 can maintain its position along the shaft axis 330 as the bendable shaft 220 bends. In addition, the shaft axis 330 maintains the same relative position and angle (e.g., the shaft axis 330 does not move) as the bendable shaft 220 bends. Thus, the shaft axis 330 can remain stationary while the bendable shaft 220 transitions from the unbent state to the bent state. Alternatively, the elongated shaft 210 can be kept in a flexed state and in the same flexed position, flexed configuration, and/or flexed orientation while the bendable shaft 220 transitions from an unbent state to a bent state. Thus, the bendable shaft 220 can bend and the customizable angle can be adjusted or set independently of the elongated shaft 210.

Figure 9:
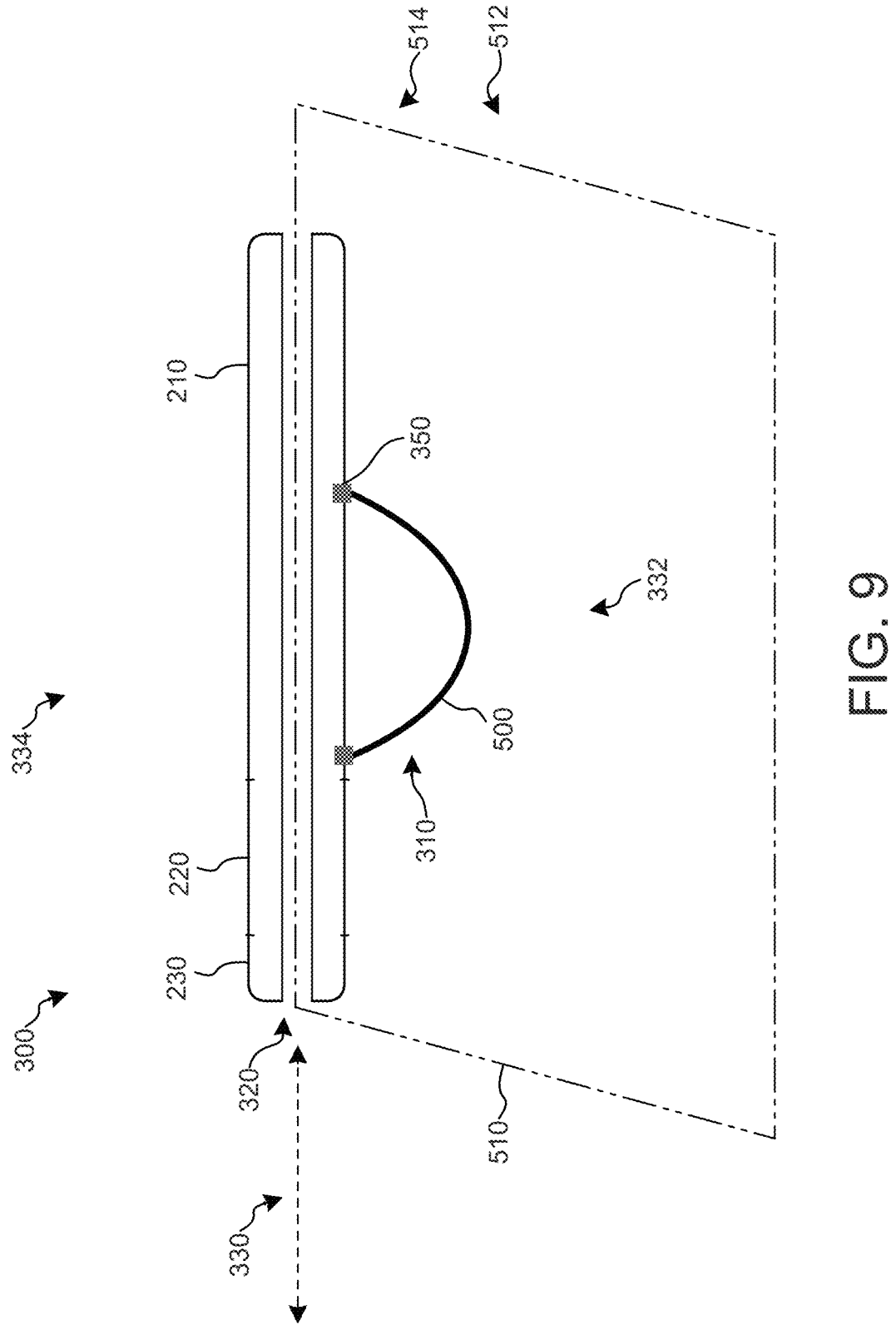
FIG. 9 is a cross-sectional view of the distal portion of the instrument port when the offset balloon is radially asymmetrically inflated according to another embodiment.

FIG. 9 is a cross-sectional view of the distal portion 300 of the instrument port 20 when the offset balloon 310 is radially asymmetrically inflated according to another alternative embodiment. The cross section is taken through plane 5-5 in FIG. 4. In this embodiment, the offset balloon 310 is only attached below 512 (e.g., on a first side of) the inflation plane 510. Since the offset balloon 310 is not attached above 514 (e.g., on a second side of) the inflation plane 510, the balloon 310 only inflates below 512 the inflation plane 510. The offset balloon 310 is only inflated on a first side 332 of the shaft axis 330 and not on a second side 334 of the shaft axis 330. A side view of this alternative embodiment would appear the same as illustrated in FIG. 8.

Figure 10:
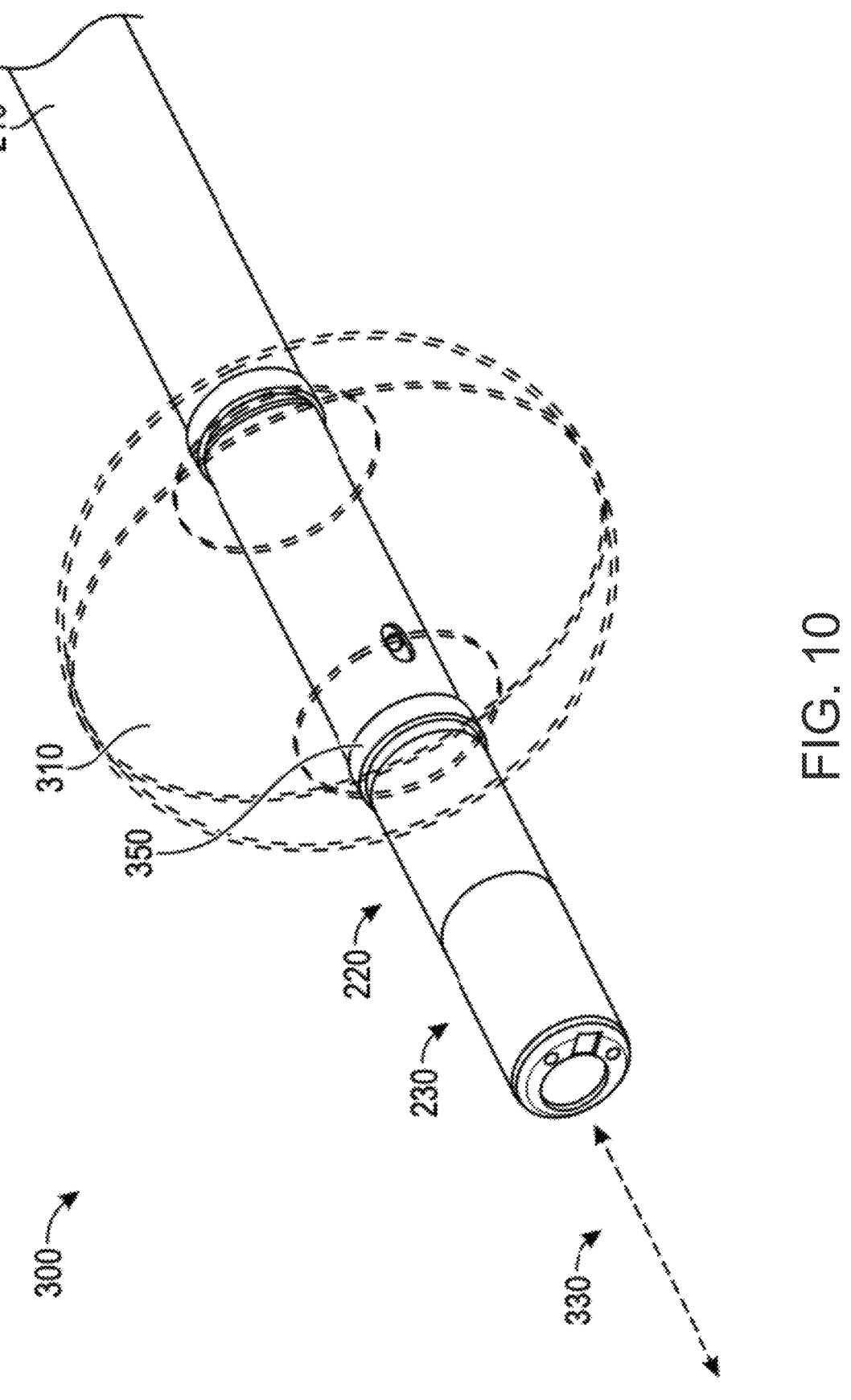
FIG. 10 is a perspective view of the distal portion of the instrument port when the offset balloon is radially symmetrically inflated according to an embodiment.
Figure 11:
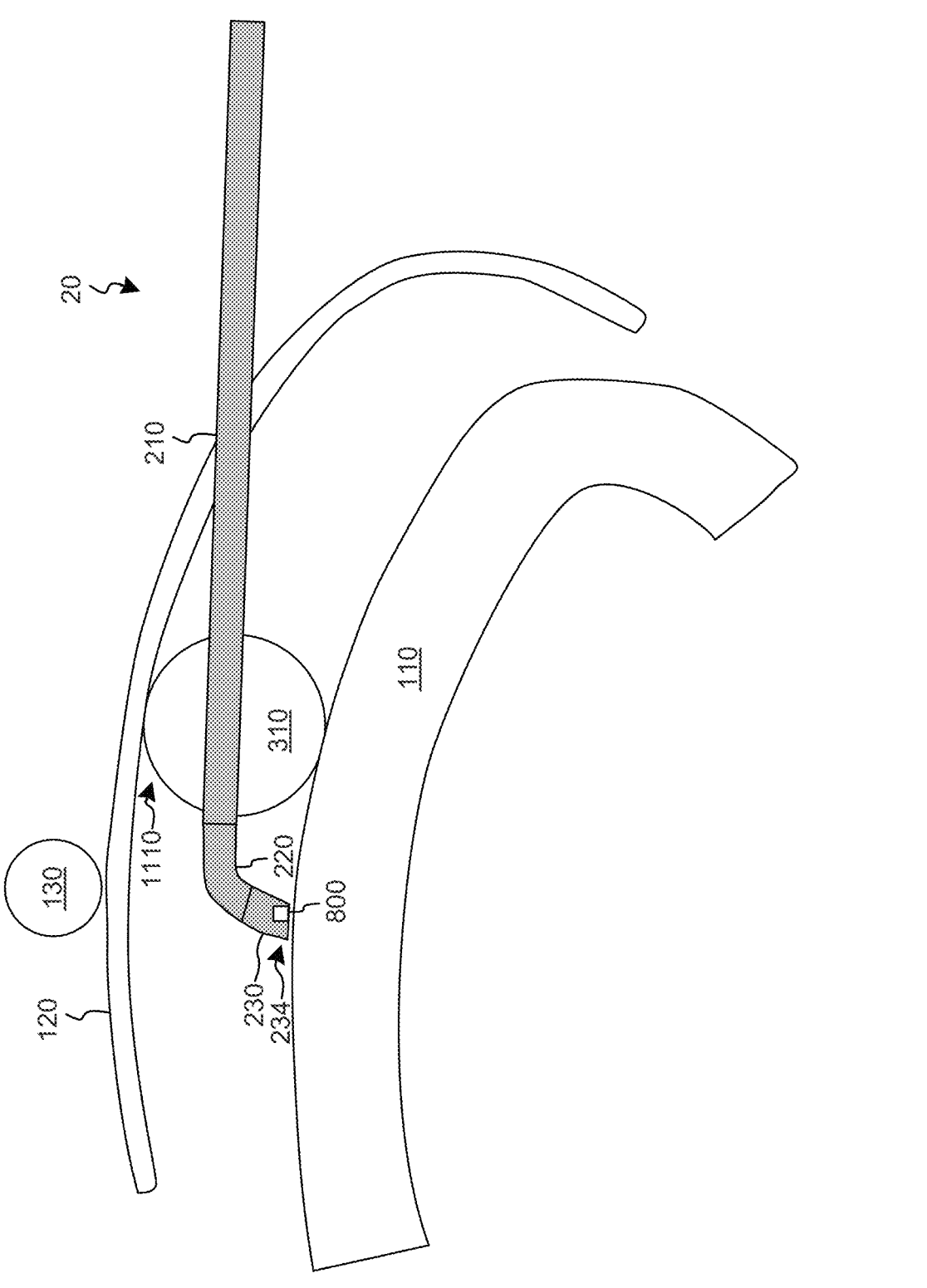
FIG. 11 illustrates a side view of the instrument port, when the offset balloon is radially symmetrically inflated, during a medical procedure according to an embodiment.

FIG. 10 is a perspective view of the distal portion 300 of the instrument port 20 when the offset balloon 310 is radially symmetrically inflated according to an embodiment. In this embodiment, the offset balloon 310 is inflated equally (or substantially equally) on the first and second sides 332, 334 of the shaft axis 330. FIG. 11 illustrates a side view of the instrument port 20 when the offset balloon 310 is radially symmetrically inflated during a medical procedure according to an embodiment. The radially-symmetric balloon provides the same or substantially the same technical advantages as the radially-asymmetric balloon. However, an advantage to the radially-asymmetric balloon is that a larger balloon can used, compared to the radially-symmetric balloon, without compromising the hemodynamics of the heart. For example, in FIG. 11 the upper portion 1110 of the radially-symmetric balloon 310 is disposed against the pericardium 120 which can generate a force or pressure on the heart tissue 110. This force or pressure is undesirable as it may affect blood flow in the heart.

As discussed above, the offset balloon 310 can be partially inflated. For example, the offset balloon 310 can have a partially-inflated volume that is a percentage of the fully-inflated volume. In a specific example, the offset balloon 310 can have a partially-inflated state in which a partially-inflated volume of the offset balloon 310 is in a range of about 10% to about 90% of the fully-inflated volume, including about 20%, about 30%, about 40%, about 50%, about 60%, about 70%, and about 80%, or any percentage or percentage between any two of the foregoing percentages. The offset balloon 310 has the fully-inflated volume when the offset balloon 310 is in the inflated state (e.g., fully-inflated state).

Figure 12:
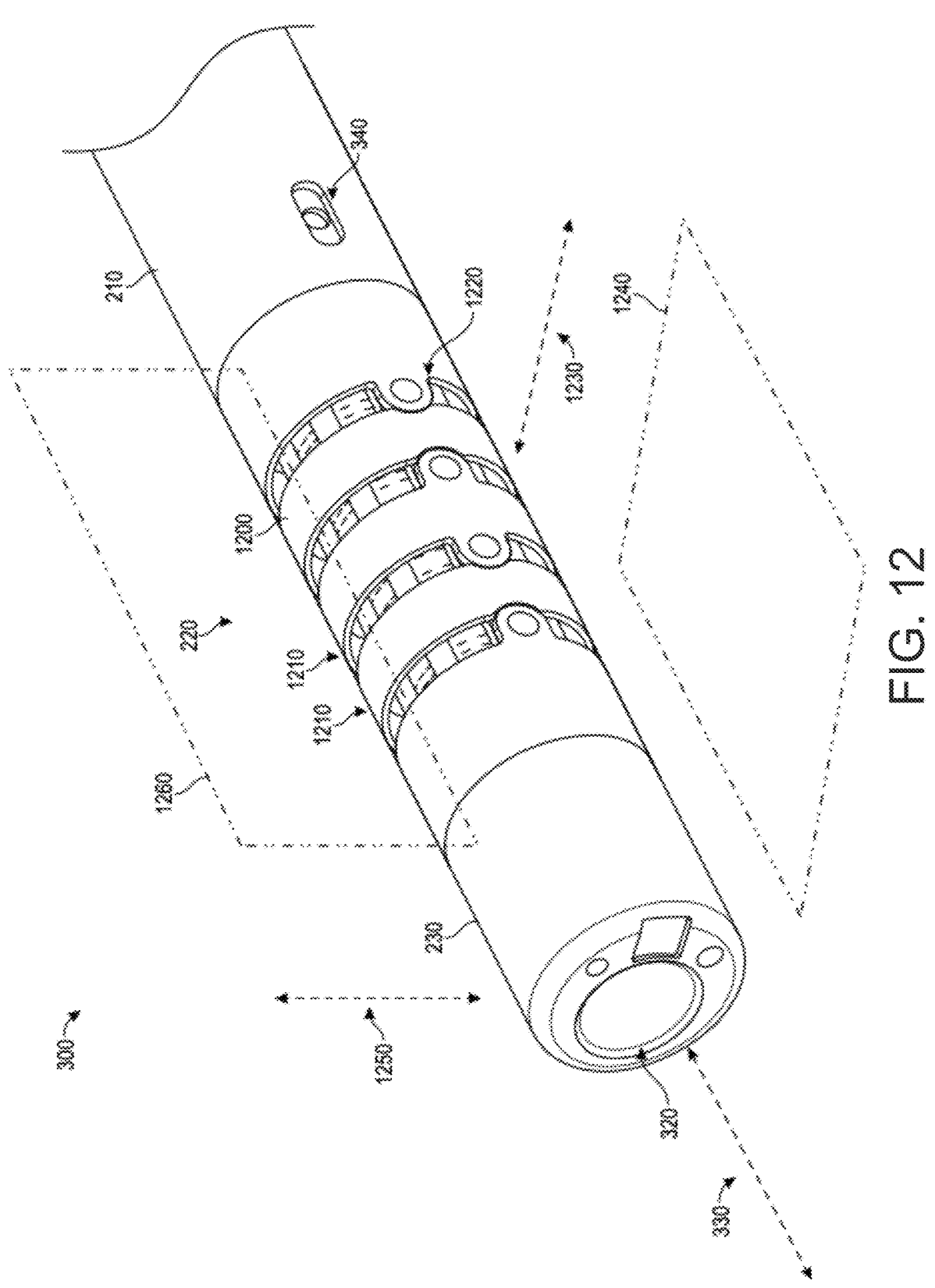
FIG. 12 is a perspective view of the distal portion of the instrument port without the offset balloon to illustrate an embodiment of the bendable shaft in the unbent state.

FIG. 12 is a perspective view of the distal portion 300 of the instrument port 20 without the offset balloon 310 to illustrate an embodiment of the bendable shaft 220 in the unbent state. The bendable shaft 220 includes a plurality of mechanical rings 1200 that are disposed concentrically along the shaft axis 330. The mechanical rings 1200 can comprise articulation links. Each neighboring pair 1210 of mechanical rings 1200 is mechanically coupled by a pair of mechanical links 1220. A respective third axis 1230 passes through each pair of mechanical links 1220. The third axis 1230 can be the same as or parallel to the width axis 360. The mechanical links 1220 provides structure that restricts the flexibility of the bendable shaft 220 within a rigidity plane 1240 defined by the shaft axis 330 and the third axis 1230. Rigidity plane 1240 can be the same as the inflation plane 510.

The mechanical rings 1200 are spaced apart along the shaft axis 330 to provide flexibility or bendability upwards or downwards with respect to a pivot axis 1250 that is orthogonal to the shaft axis 330 and the third axis 1330. The pivot axis 1250 and the shaft axis 330 define a pivot plane 1260 in which the bendable shaft 220 can bend upwards or downwards. Rigidity plane 1240 and pivot plane 1260 are mutually orthogonal.

The mechanical rings 1200 and mechanical links 1220 can be formed of metal (e.g., stainless steel or titanium) or plastic (e.g., a polyamide, a polyetherimide, and/or another plastic). In an embodiment, the proximal end of the bendable shaft 220 is welded to the distal end of the elongated shaft 210. In addition, the distal end of the bendable shaft 220 can be bonded to the proximal end of the steerable tip 230.

Figure 13:
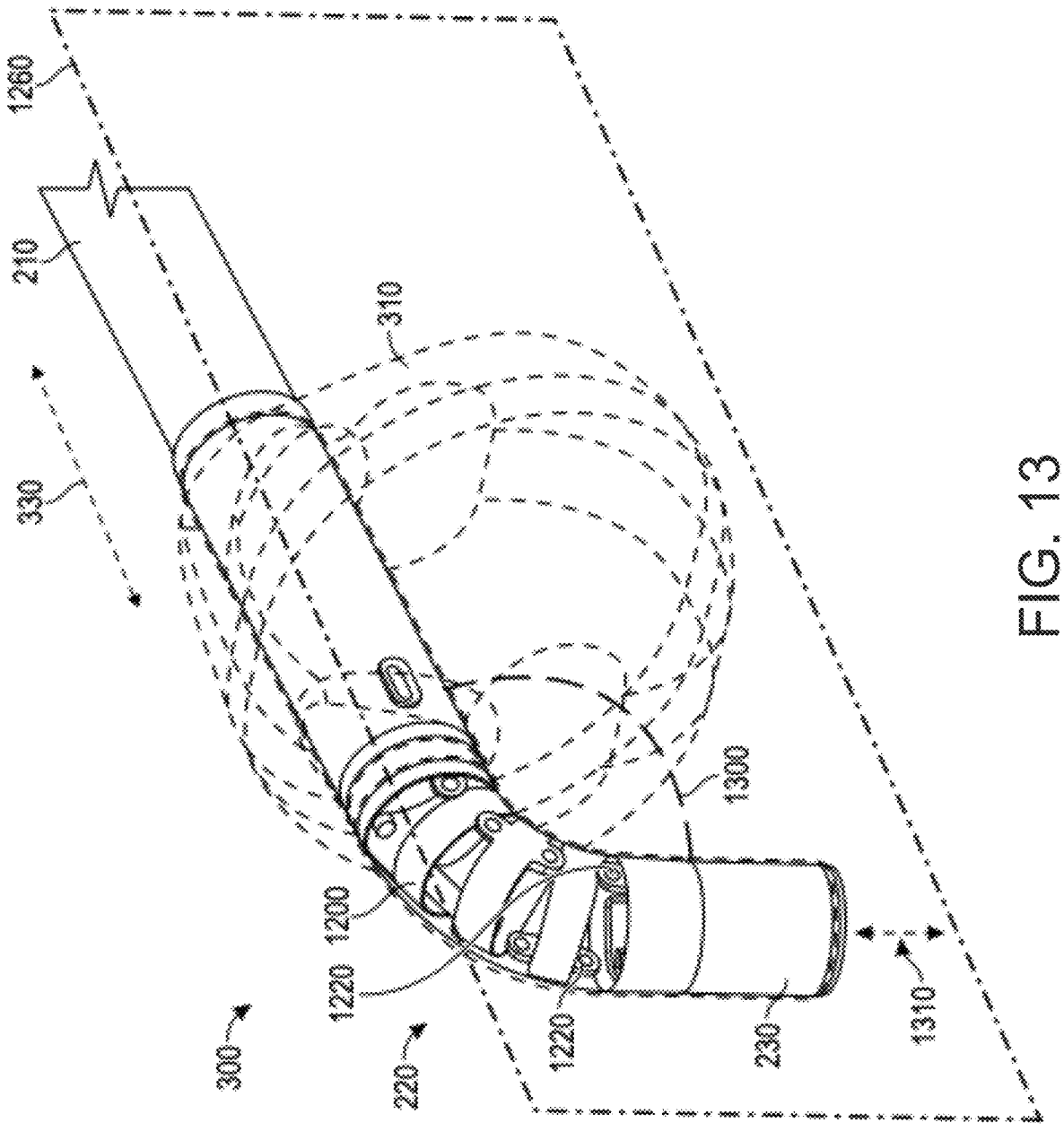
FIG. 13 is a perspective view of the distal portion of the instrument port with the offset balloon to illustrate an embodiment of the bendable shaft in the bent state.

FIG. 13 is a perspective view of the distal portion 300 of the instrument port 20 with the offset balloon 310 to illustrate an embodiment of the bendable shaft 220 in the bent state. In the bent state, the mechanical rings 1200 are spaced further apart on the side of the bendable shaft 220 that is away from the direction of bending and the mechanical rings 1200 are spaced closer together on the side of the bendable shaft 220 that is towards from the direction of bending. The bendable shaft 220 can be adjusted in the bendable state to form a customizable angle 1300 of the steerable tip 230 with respect to the elongated shaft 210. The customizable angle 1300 can be measured between the shaft axis 330 and a tip axis 1310 that extends through the working channel 320 in the steerable tip 230. In the unbent state, the tip axis 1310 and the shaft axis 330 are collinear.

FIGS. 12 and 13 also illustrate that the bendable shaft 220 can bend without affecting the position, shape, orientation, and/or behavior of the elongated shaft 210. For example, the elongated shaft 210 maintains its position along the shaft axis 330 as the bendable shaft 220 bends. In addition, the shaft axis 330 maintains the same relative position and angle (e.g., the shaft axis 330 does not move) as the bendable shaft 220 bends. Thus, the shaft axis 330 can remain stationary while the bendable shaft 220 transitions from the unbent state to the bent state. Alternatively, the elongated shaft 210 can be kept in a flexed state while the bendable shaft 220 transitions from an unbent state to a bent state.

Figure 18:
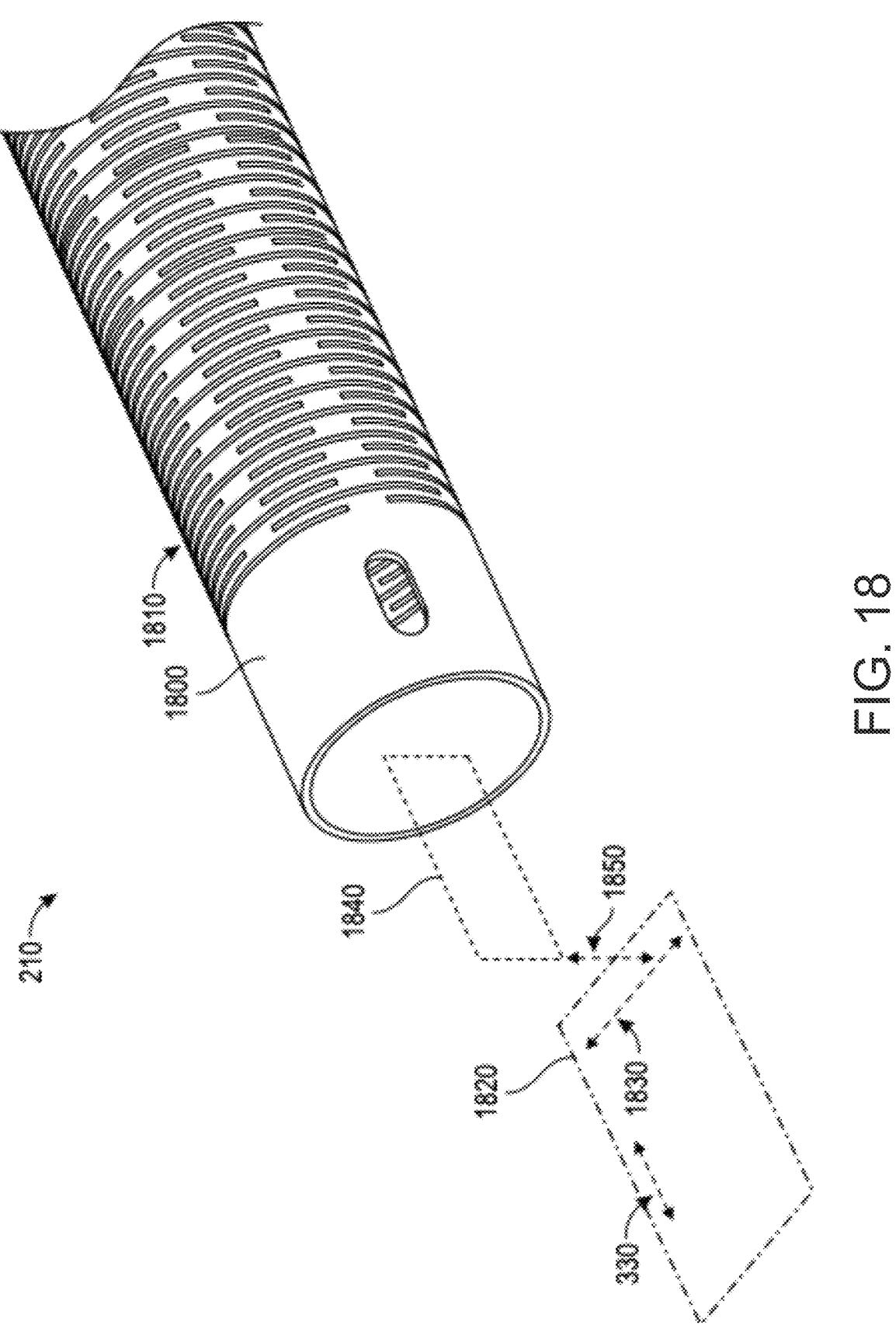
FIG. 18 is an isolated perspective view of the elongated shaft according to an embodiment.
Figure 19:
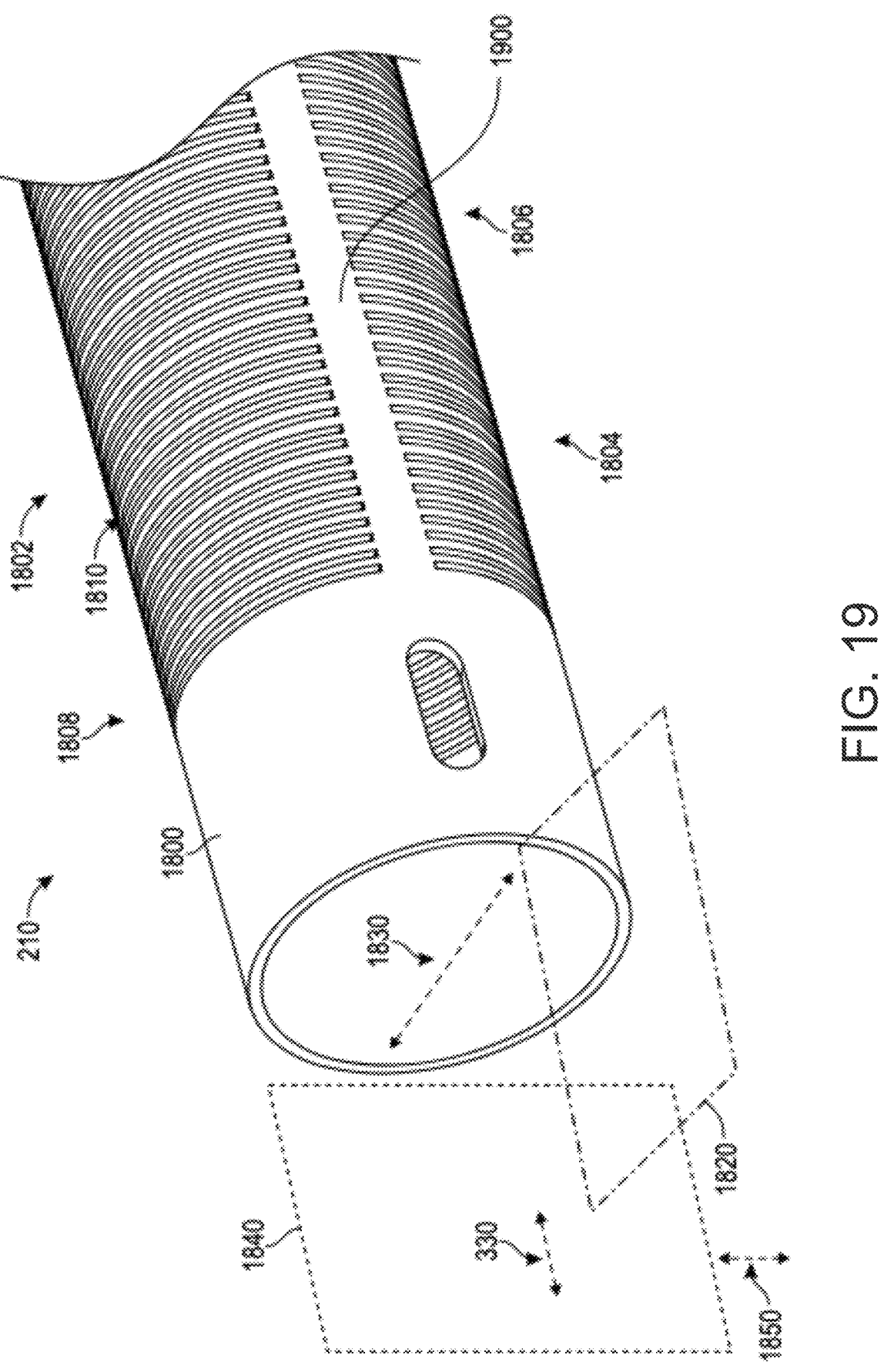
FIG. 19 is an isolated perspective view of the elongated shaft according to another embodiment.

It is also noted that the elongated shaft 210 is flexible in some embodiments (e.g., as described herein for example in FIGS. 18 and 19). In the unflexed state, the elongated shaft 210 extends along the shaft axis 330. In the flexed state, some or all of the elongated shaft 210 does not extend along the shaft axis 330. For example, the elongated shaft 210 can be bent or curved in the flexed state such as to be positioned around an anatomical feature (e.g., the heart). In either case (the flexed or unflexed state), the bendable shaft 220 can remain stationary (e.g., in the same flexed or unflexed configuration, flexed or unflexed position, flexed or unflexed state, flexed or unflexed orientation, etc.) while the bendable shaft 220 transitions from the unbent state to the bent state. Thus, the bendable shaft 220 can bend and the customizable angle can be adjusted or set independently of the elongated shaft 210.

Figure 14:
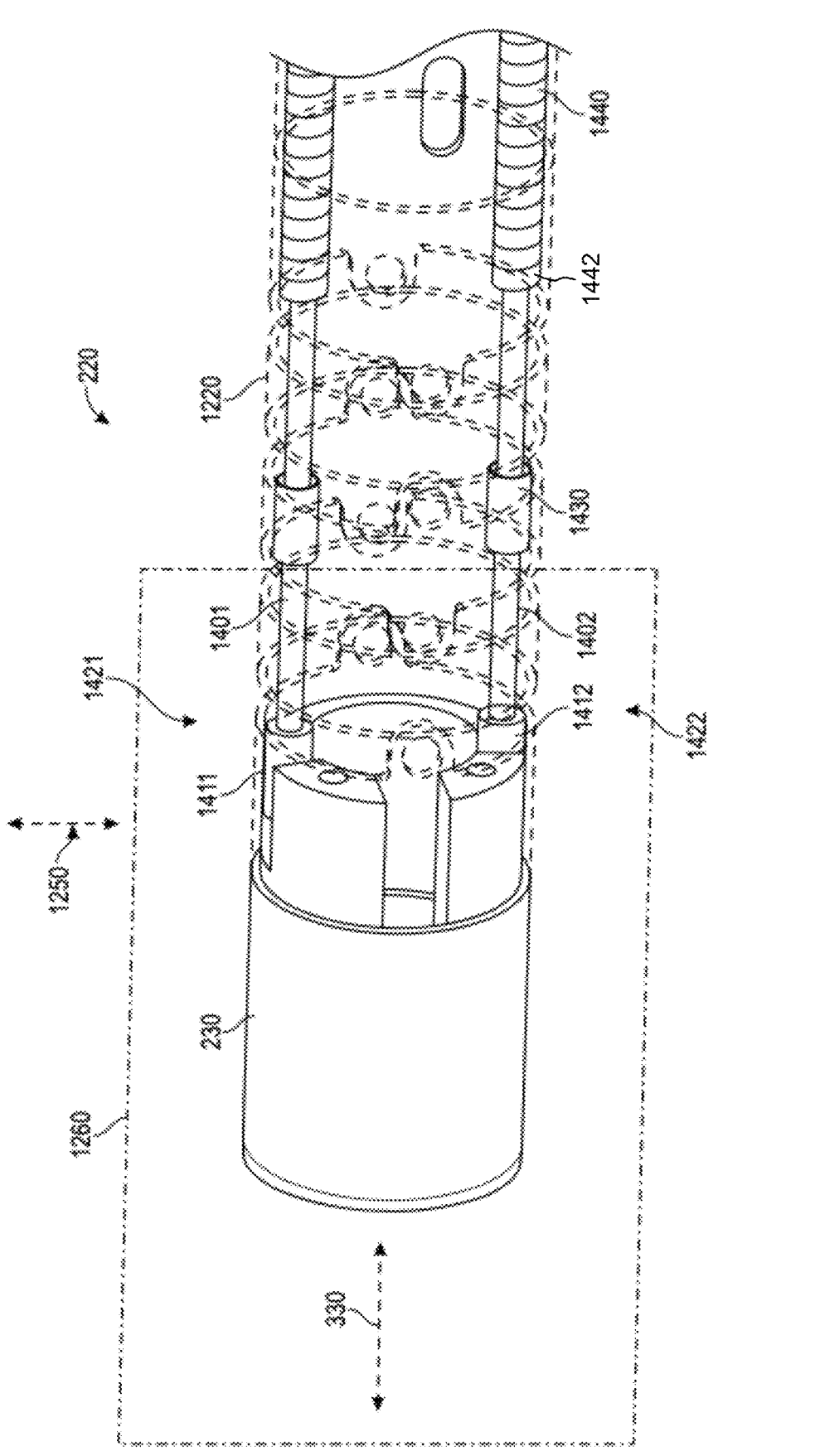
FIG. 14 is a perspective view of the bendable shaft and steerable tip in an unbent state according to an embodiment.

FIG. 14 is a perspective view of the bendable shaft 220 and steerable tip 230 in an unbent state according to an embodiment. In this view, the mechanical rings 1200 and mechanical links 1220 are partially transparent to illustrate first and second wires 1401, 1402 in the bendable shaft 220. A first end 1411 of the first wire 1401 is attached to a first side 1421 (e.g., at an internal surface) of the distal end of the bendable shaft 220. A second end 1412 of the second wire 1402 is attached to a second side 1422 (e.g., at an internal surface) of the distal end of the bendable shaft 220. The first and second ends 1411, 1412 can be crimped and/or welded to the distal end of the bendable shaft 220. In the unbent state, the first and second ends 1411, 1412 are attached to opposing sides 1421, 1422 of the bendable shaft 220 along the pivot axis 1250.

The first and second wires 1401, 1402 extend to the handle 200 where they can be pulled (e.g., by one or more levers) to bend the bendable shaft 220 in a corresponding direction within the inflation plane 1260. For example, the first wire 1401 can be pulled to bend the bendable shaft 220 upwards (e.g., in a first direction corresponding to first side 1421). Likewise, the second wire 1402 can be pulled to bend the bendable shaft 220 downwards (e.g., in a second direction corresponding to second side 1422). Each wire 1401, 1402 can pass through one or more guide sleeves 1430. In an embodiment, the first and second wire 1401, 1402 can comprise first and second wire ropes.

Figure 15:
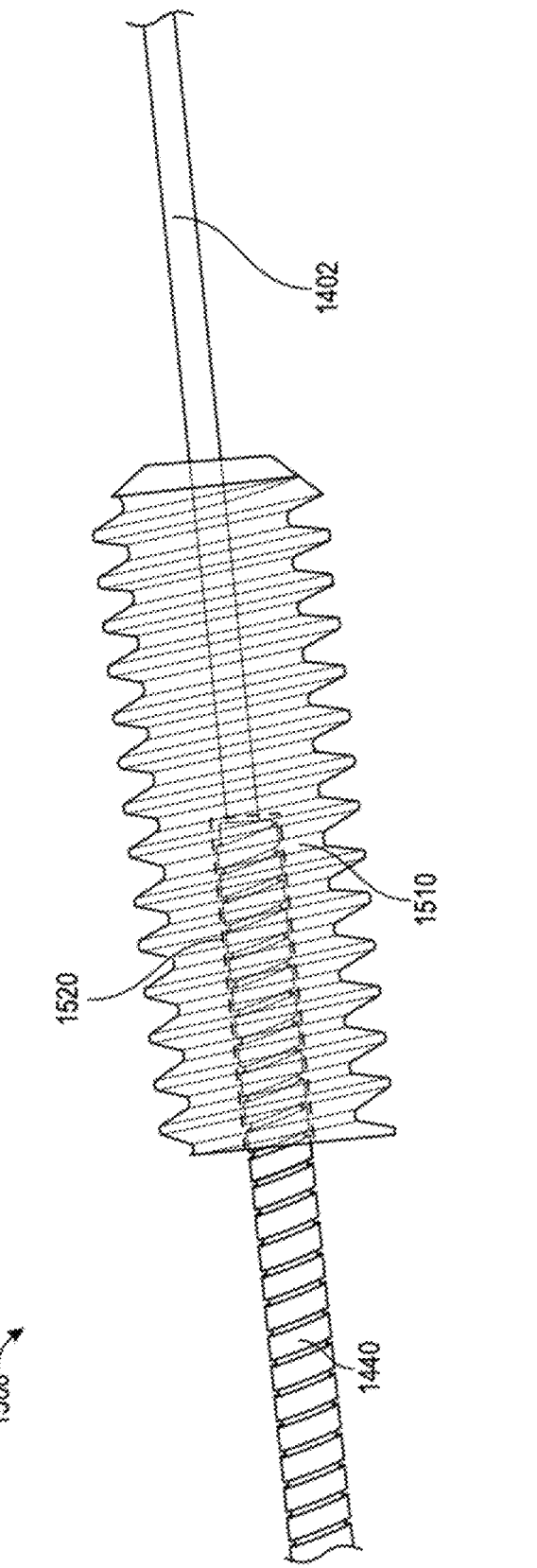
FIG. 15 is a perspective view of a wire-tension adjuster according to an embodiment.

Each wire 1401, 1402 can optionally pass through and/or can be attached to a tightly-wound coil 1440 which is part of a wire-tension adjuster 1500 as illustrated in FIG. 15. A distal end 1442 of the tightly-wound coil 1440 is fixedly attached (e.g., welded) to a mechanical ring 1200 (e.g., a mechanical ring 1200 towards the proximal end 202 of the instrument port 20). The wire-tension adjuster 1500 includes the tightly-wound coil 1440 and a tension adjuster 1510. The tension adjuster 1510 is attached to an adjuster plate 2440 (FIG. 24) in the handle 200. The tension adjuster 1510 includes a counterbore 1520 that includes internal threads that engage the external threads on the tightly-wound coil. The tension adjuster 1510 can be rotated in a first direction to increase tension on the wire 1402 and in a second direction to decrease tension on the wire 1402. Though the wire-tension adjuster 1500 is illustrated with respect to wire 1402, an identical wire-tension adjuster 1500 can be used with wire 1401.

Figure 16:
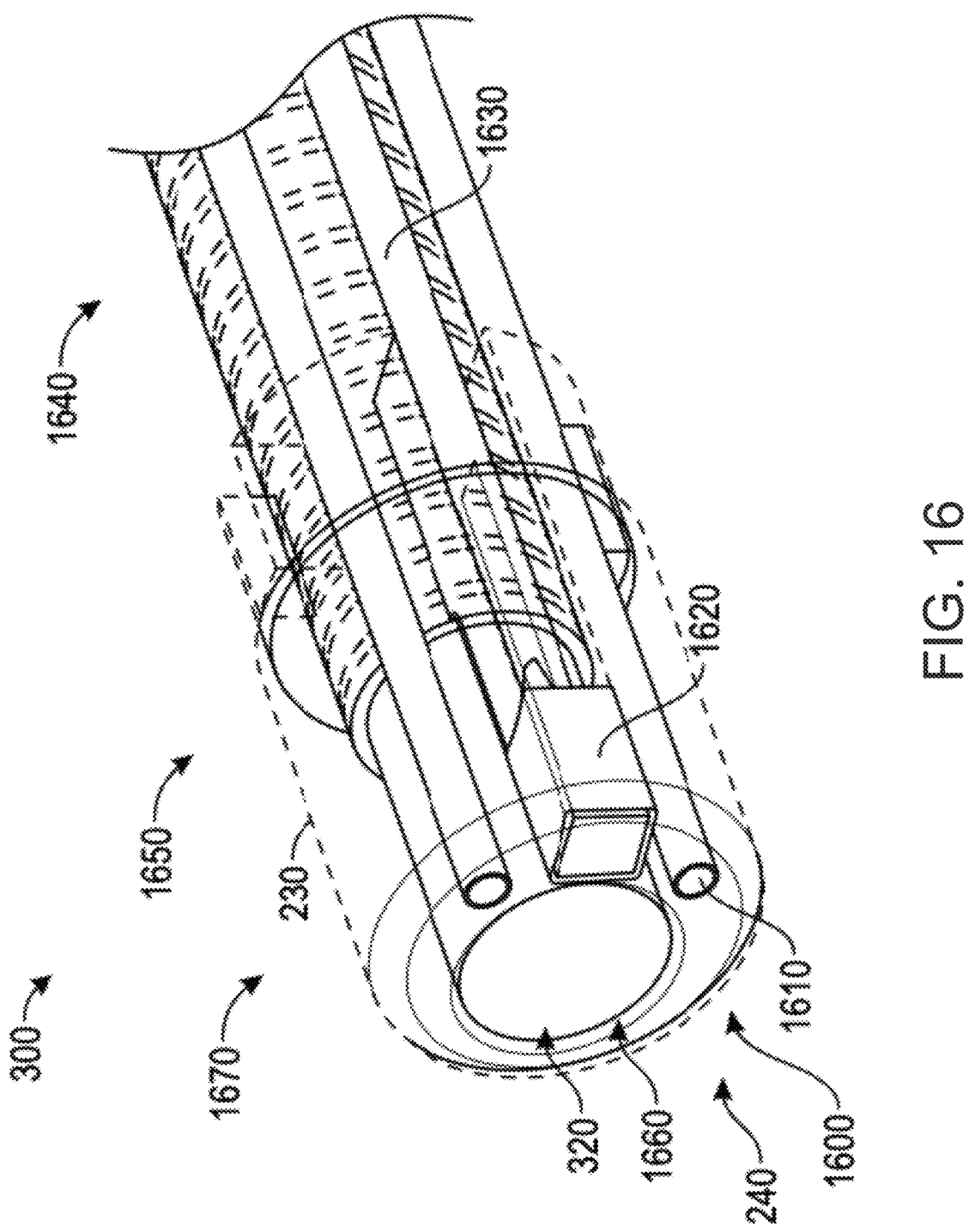
FIG. 16 is a perspective view of the distal portion of the instrument port according to an embodiment.

FIG. 16 is a perspective view of the distal portion 300 of the instrument port 20 according to an embodiment. In this view, the steerable tip 230 is partially transparent and the bendable shaft 220 is removed to illustrate an imaging system 1600 disposed at the distal end 204 of the instrument port 20 (and the distal end of the distal tip 230). The imaging system 1600 includes first and second light emitters 1610 disposed around a camera 1620. Each light emitters 1610 can include a fiber optic cable or a bundle of fiber optical cables. The fiber optics are optically coupled to a light (e.g., an LED light, an incandescent light, a laser, or another light) at their proximal end and transmit the light through the fiber optics, which is output at the distal end 204 of the instrument port 20. In an alternative embodiment, the light emitters 1610 can include one or more lights (e.g., LEDs) that are disposed in the steerable tip 230 to output the light at the distal end 204 of the instrument port 20. Additional or fewer light emitters 1610 can be included in other embodiments.

The camera 1620 includes a light sensor that is sensitive to one or more frequencies of light emitted from the light emitters 1610. The camera 1620 is electrically coupled to a cable 1630 that extends to the proximal end 202 of the instrument port 20 where the cable 1630 can be connected to a controller. The controller can include the light(s) for the light emitters 1610. The light emitted by the light emitters 1610 can be modified by the controller by altering its intensity, using analog controls on the controller or digital controls in the display software, and emission spectrum by well-known means such as polarization and/or band-pass filtering, etc. The camera 1620 can be used to acquire still or moving (e.g., video) image data of the region in front of (e.g., distal to) the distal end 204 of the instrument port 20. For example, the camera 1620 can be used to acquire still or moving image data of the heart tissue 110, the pericardium 120, and the lesion 130 as it is formed. These images can be used to train advanced image feature detection algorithms such as in machine learning techniques. In some embodiments, the image data can be used to automatically detect the characteristics of the lesion 130 (e.g., size, color, etc.) to automatically stop ablation when the lesion 130 has predetermined characteristics (e.g., size, color, etc.). The camera 1620 can acquire 2D or 3D image data (e.g., 3D image data can include stereo still images and/or stereo video images). Imaging system 1600 can be the same as or different than imaging system 800.

A working tube 1640 is disposed in the bendable shaft 220 and at least a proximal portion 1650 of the steerable tip 230. The working tube 1640 and a tip channel 1660 defined in a distal portion 1670 of the steerable tip 230 form the working channel 320. The working tube 1640 can extend to the handle 200 and/or the proximal end 202 of the instrument port 20. The working tube 1640 can also extend to the distal portion 1670 of the steerable tip 230 to replace some or all of the tip channel 1660.

Figure 17:
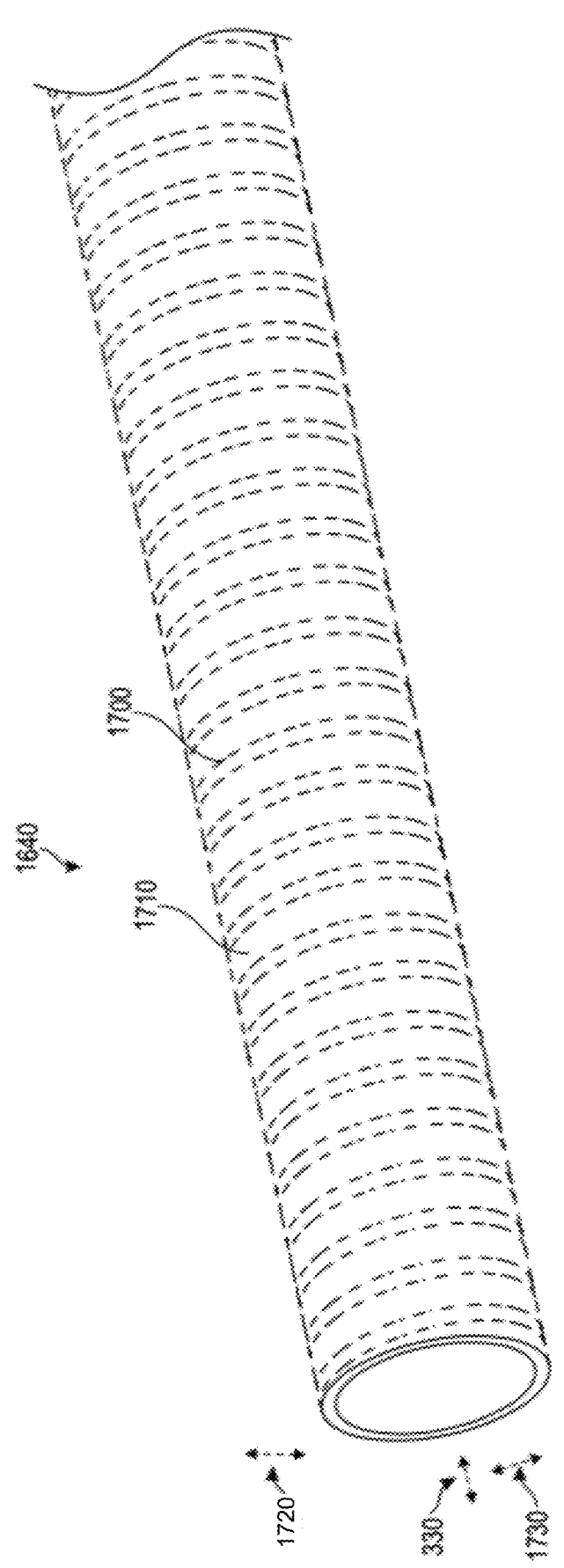
FIG. 17 is an isolated perspective view of the working tube according to an embodiment.

FIG. 17 is an isolated perspective view of the working tube 1640 according to an embodiment. The working tube 1640 includes a helical or spiral wire 1700 that flexibly structurally supports a working tube body 1710. The working tube body 1710 can comprise a polyether block amide (e.g., PEBAX®) and/or another material with an ethylene propylene (FEP) liner and/or a polytetrafluoroethylene (PTFE) liner. FEP and/or PTFE can provide a relatively smooth surface through which to insert a medical device (e.g., an ablation catheter such as ablation catheter 100). In the relaxed state, the working tube 1640 extends along and/or parallel to the shaft axis 330. The working tube 1640 can flex and/or bend with respect to one or more axes that are orthogonal to the shaft axis 330, such as axes 1720 (e.g., parallel to the height of working tube 1640) and/or 1730 (e.g., parallel to the width of working tube 1640).

FIG. 18 is an isolated perspective view of the elongated shaft 210 according to an embodiment. The elongated shaft 210 comprises an elongated tube 1800 that extends along and/or parallel to the shaft axis 330 in a relaxed state. The elongated tube 1800 can be formed of metal (e.g., stainless steel, titanium, and/or another metal), plastic, and/or another material. A plurality of slits or apertures 1810 are defined in the flexible tube 1800 to create flexibility in the elongated tube 1800. The slits 1810 can be formed by machining, laser etching, or another technique. The slits 1810 can be configured to provide flexibility (e.g., passive flexibility) with respect to a first plane 1820 defined by the shaft axis 330 and a width axis 1830 that is orthogonal to the shaft axis 330. The width or diameter of the elongated tube 1800 can be measured with respect to the width axis 1830. The slits 1810 can also provide flexibility (e.g., passive flexibility) with respect to a second plane 1840 defined by the shaft axis 330 and a height axis 1850 that is orthogonal to the shaft axis 330 and to the width axis 1830. The height or diameter of the elongated tube 1800 can be measured with respect to the height axis 1850. In the unflexed state (as illustrated in FIG. 18), the elongated tube 1800 extends along the shaft axis 330.

The slits 1810 form a pattern such as an interrupted spiral pattern that can provide flexibility within planes 1820, 1840. In another embodiment, the slits 1810 are arranged as a plurality of fins that extend circumferentially on first and second sides 1802, 1804 of the elongated tube 1800, as illustrated in FIG. 19. A gap 1900 is disposed on a third side 1806 of the elongated tube 1800 between the slits 1810 on the first side 1802 and the slits 1810 on the second side 1804 of the elongated tube 1800. A second gap 1900 is disposed on a fourth side 1808 of the elongated tube 1800 between the slits 1810 on the first side 1802 and the slits 1810 on the second side 1804 of the elongated tube 1800. The gaps 1900 on the third and fourth sides 1806, 1808 are aligned and with respect to the width axis 1830. The gaps 1900 correspond to regions of solid elongated tube 1800 (e.g., that do not include slits 1810) that is not flexible (e.g., stiff) compared to the regions of elongated tube 1800 that include the slits 1810. Thus, the elongated tube 1800 in FIG. 19 is flexible with respect to plane 1840 but is not flexible with respect to plane 1820.

Figure 20:
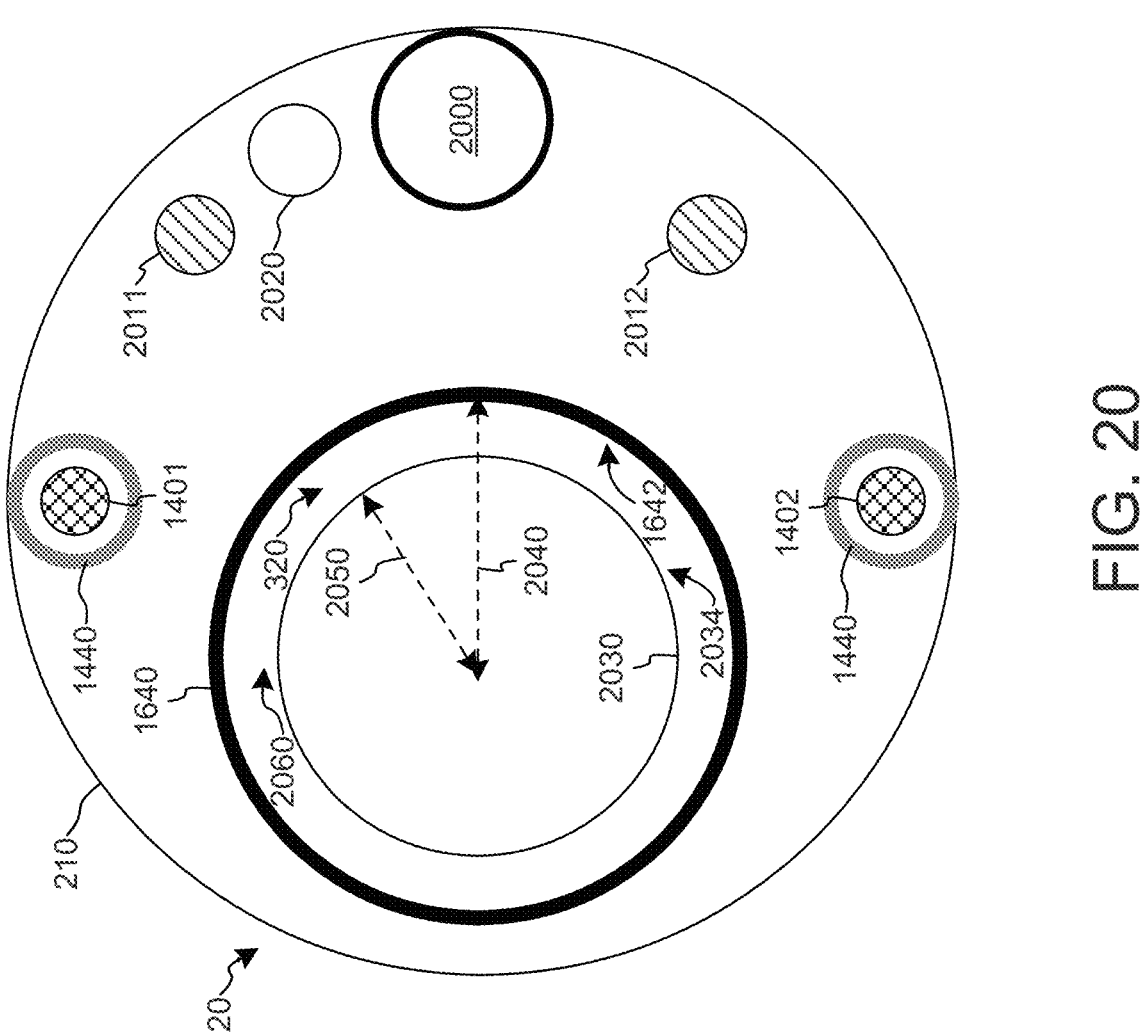
FIG. 20 is a cross-sectional view of the elongated shaft.

FIG. 20 is a cross-sectional view of the elongated shaft 210 through line 20-20 in FIG. 3 to illustrate the relative arrangement of certain components described herein. The cross-sectional view illustrates an example arrangement of the first and second wires 1401, 1402, the optional tightly-wound coils 1440, a fluid tube 2000, the working tube 1640, first and second fiber optic cables 2011, 2012, and an imaging cable 2020. The fluid tube 2000 is fluidly coupled to the fluid port 340 to provide and/or receive fluid to/from the offset balloon 310. In an example, the fluid tube 2000 includes a hole that is disposed against the fluid port 340, and a distal end of the fluid tube 2000 is capped or sealed to force fluid flow into or out of the fluid port 340 to/from the offset balloon 310 (e.g., to define a closed fluid path therebetween). The first and second fiber optic cables 2011, 2012 are electrically coupled to first and second light emitters 1610. In an embodiment, the first and second light emitters 1610 comprise the first and second fiber optic cables 2011, 2012. The imaging cable 2020 is electrically coupled to the camera 1620 to send image data from the camera 1620 to an external controller (or other device), to send commands from the external controller to the camera 1620 (e.g., to adjust the focus of the camera), and/or to provide electrical power to the camera 1620. In an alternative embodiment, the camera 1620 can be battery-powered and/or can be in wireless communication with the external controller (or other device).

An optional medical device 2030 (e.g., an ablation catheter such as ablation catheter 100) is inserted in the working channel 320 inside the working tube 1640. The working tube 1640 is configured to have a radius 2040 (e.g., a working tube radius) that is greater than a radius 2050 of the medical device 2030 (e.g., a medical device radius). A fluid channel 2060 is formed between the external surface 2034 of the medical device 2030 and the internal surface 1642 of the working tube 1640. The fluid channel 2060 can be used to flush (e.g., with a liquid such as saline or semi-saline water) the external surface 2034 of the medical device 2030 and/or the surgical site during and/or prior to the medical procedure. In addition or in the alternative, the fluid channel 2060 can be fluidly coupled to a vacuum source to apply a vacuum to the external surface 2034 of the medical device 2030 and/or the surgical site, such as to remove debris and/or liquid (e.g., saline or semi-saline water, blood, etc.) therefrom.

Figure 21:
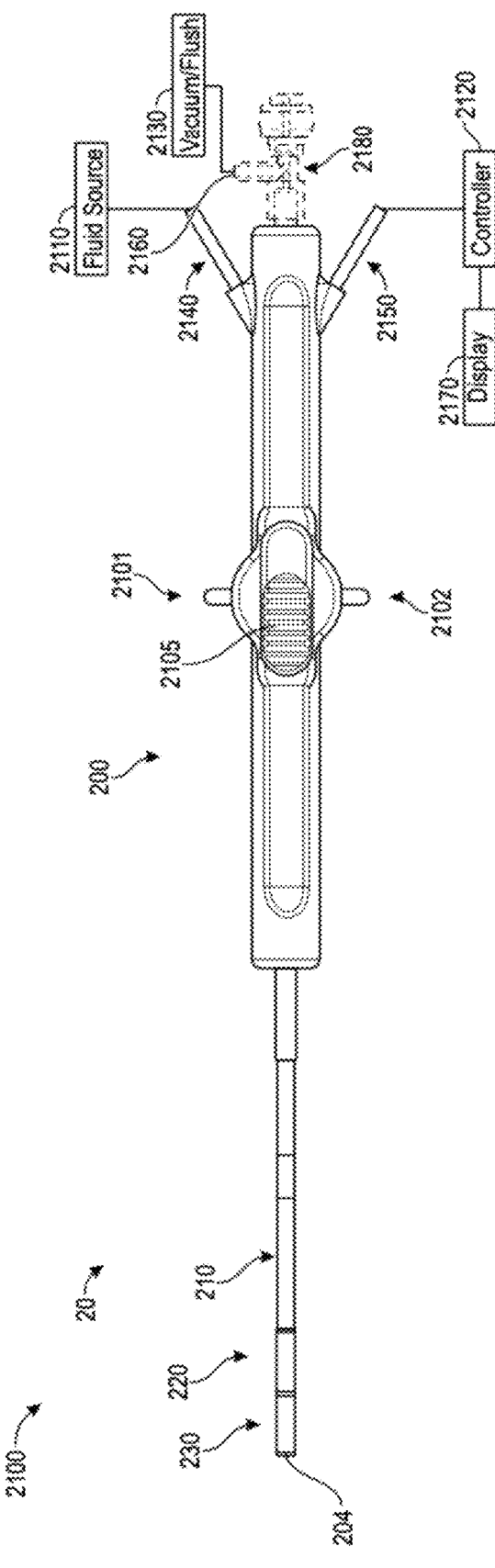
FIG. 21 is a top view of an instrument port system according to an embodiment.

FIG. 21 is a top view of an instrument port system 2100 according to an embodiment. The instrument port system 2100 includes instrument port 20, a fluid source 2110, a microprocessor-based controller 2120, and a vacuum/liquid flush source 2130. The elongated shaft 210 of the instrument port 20 is broken in this figure to fit instrument port 20 within the page. The handle 200 includes first and second levers 2101, 2102 that are mechanically coupled to the first and second wires 1401, 1402, respectively. Pressing the first lever 2101 towards the proximal end 202 of the instrument port 20 creates tension in the first wire 1401 to bend the bendable shaft 220 in a first direction. Pressing the first lever 2101 towards the proximal end 202 of the instrument port 20 can also release tension in the second wire 1402. Pressing the second lever 2102 towards the proximal end 202 of the instrument port 20 creates tension in the second wire 1402 to bend the bendable shaft 220 in a second direction. Pressing the second lever 2102 towards the proximal end

202 of the instrument port 20 can also release tension in the first wire 1401. The first and second levers 2101, 2102 can be the same as lever(s) 240. A mechanical lock 2105 can lock the relative position of the first and second levers 2101, 2102 which can fix the tension on the respective wire 1401, 1402 thereby locking the orientation (e.g., angle 1300) of the bendable shaft 220 and steerable tip 210. The mechanical lock 2105 is positioned in a locked state (e.g., towards the distal end 204) in FIG. 21. The mechanical lock 2105 can also be moved towards the proximal end 202 to transition to an unlocked state.

A handle fluid port 2140 is formed in the handle 200 (e.g., at a proximal end of handle 200). The handle fluid port 2140 is fluidly coupled to the fluid source 2110 and to the fluid tube 2000, which is fluidly coupled to the fluid port 340 and to the offset balloon 310. The fluid source 2110 can releasably retain a predetermined volume of liquid or gas for inflating the offset balloon 310. The fluid source 2110 can comprise a syringe, a tank, or other apparatus that can releasably retain a fluid. The fluid source 2110 can also receive the predetermined volume of liquid or gas from the offset balloon 310 to deflate the offset balloon 310.

An optical system port 2150 is also formed in the handle 200 (e.g., at the proximal end of handle 200). One or more cables can be inserted through the optical system port 2150 and can extend to the imaging system 1600. For example, the fiber optic cables 2011, 2012 and/or the imaging cable 2020 can be inserted through the optical system port 2150. Proximal ends of the cables can be optically and/or electrically coupled to the controller 2120. The controller 2120 can include a light (e.g., LED, laser, etc.) that is optically coupled to the fiber optic cables 2011, 2012. The controller 2120 can also include a power source for the camera 1620 and/or a microprocessor-based computer that is in signal communication with the camera 1620 to send commands thereto and to receive image data therefrom. The controller 2120 can optionally be in electronic communication with a computer display 2170 that can display images that correspond to the image data acquired by the imaging system 1600.

In some embodiments, the controller 2120 is configured to improve and/or analyze the image data acquired by the imaging system 1600. In addition to the image itself, additional useful information can be recorded, such as the time of acquisition of each still or moving image. As an example of image data improvement, the controller 2120 can apply one or more well-known image analytic algorithms to filter noise and/or reduce glare from the each still or moving image series, aggregate still images or sections of moving images to enhance certain features, apply smoothing, sharpening, edge detection, etc. kernels to still or moving images and/or decompose the images into various colors or wavelengths optimized for feature detection.

The controller 2120 can be configured to automatically detect (e.g., in real time) certain anatomical features that may be relevant to a planned medical procedure. Optimal combinations of illumination from the light emitter, acquisition using the camera, and/or processing in the controller 2120 can be selected to enhance the detection of relevant features. In an epicardial ablation procedure, the controller 2120 can be configured to automatically detect (e.g., in real time) the heart tissue 110, the pericardium 120, coronary arteries, fat pads, and/or the phrenic nerve 140. The controller 2120 can use artificial intelligence, image recognition, machine learning inferencing, and/or other methods to automatically detect the anatomical features. When enabled, such detected features can be digitally identified on the display system as superimposed on the still or moving imagery captured or in real-time acquisition from the camera. Additionally or alternatively, the controller 2120 can be configured to automatically detect and/or track in real time a lesion created with any ablation technology (e.g., RF, cryoablation, needle ablation, laser ablation, and/or electroporation) during epicardial ablation. In an embodiment, the controller 2120 can be configured to automatically detect the size, color, and/or other characteristics or properties of the lesion 130 in real time during epicardial ablation. The controller 2120 can also be in electrical communication with the medical device 2030 (e.g., ablation catheter) and configured to stop epicardial ablation in real time when the lesion 130 has reached a predetermined size, color, and/or characteristics or properties, such as by using artificial intelligence, image recognition, and/or other methods.

Figure 27:
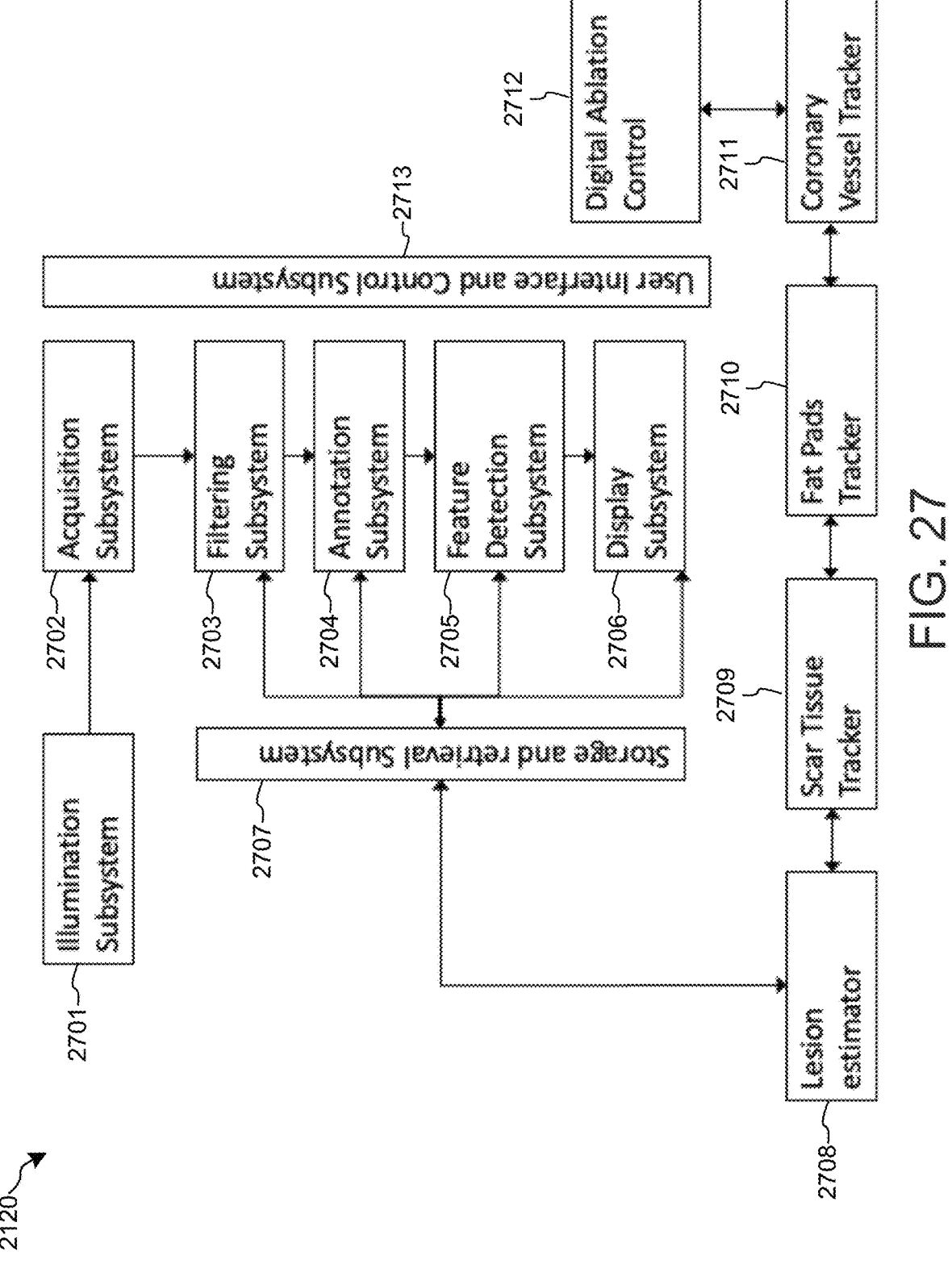
FIG. 27 is a block diagram of subsystems that can be included in the controller.

The controller 2120 can include and/or can be programmed to include one or more subsystems, controllers, and/or features as illustrated in FIG. 27. For example, the controller 2120 can include and/or can be programmed to include an illumination subsystem 2701, an acquisition subsystem 2702, a filtering subsystem 2703, an annotation subsystem 2704, a feature detection subsystem 2705, a display subsystem 2706, a storage and retrieval subsystem 2707, a lesion estimator subsystem 2708, a scar tissue tracker subsystem 2709, a fat pads tracker subsystem 2710, a coronary vessel tracker subsystem 2711, an ablation control subsystem 2712, and/or a user interface and control subsystem 2713.

The controller 2120 can control the lights in the light emitters 1610 using the illumination subsystem 2701 or the controller 2120 can generate light (e.g., a light source) using the illumination subsystem 2701 which can be transmitted to the light emitters 1610 over optical fibers. In addition, the controller can control the camera 1620 and receive image data using the image acquisition subsystem 2702. The received image data can pass through the filtering subsystem 2703, annotation subsystem 2704, feature detection subsystem 2705, and display subsystem 2706. For example, the filtering subsystem 2703 can filter noise and/or reduce glare from the image data. The annotation subsystem 2704 can be used to automatically annotate image data to indicate any anatomical features that are automatically detected. The annotation subsystem 2704 can also automatically add the date, time, patient name or ID, and/or other information to the image data. The annotation subsystem 2704 can also manually add information based on user input from user interface and control subsystem 2713.

The feature detection subsystem 2705 can include artificial intelligence, image recognition, machine learning inferencing, and/or other methods to automatically detect (e.g., in real time) anatomical features and/or other information. The image data can be automatically annotated to indicate the detected features using annotation subsystem 2704. The feature detection subsystem 2705 can detect the anatomical features and/or other information based on size, color, shape, and/or other characteristics of the anatomical features. In some embodiments, the feature detection subsystem 2705 can be programmed with the target region for the medical procedure which can improve detection speed (e.g., so the feature detection subsystem 2705 does not attempt to detect an anatomical feature that is not near the target region for the medical procedure).

The display subsystem 2706 can be used to generate images after the received image data has passed through the filtering subsystem 2703, the annotation subsystem 2704, and/or the feature detection subsystem 2705. The storage and retrieval subsystem 2707 can be used to store and/or retrieve image data, such as storing image data in and/or retrieving data from memory accessible to the controller 2120 (e.g., internal and/or external memory which can include network-accessible memory).

Figures 28A, 28B:
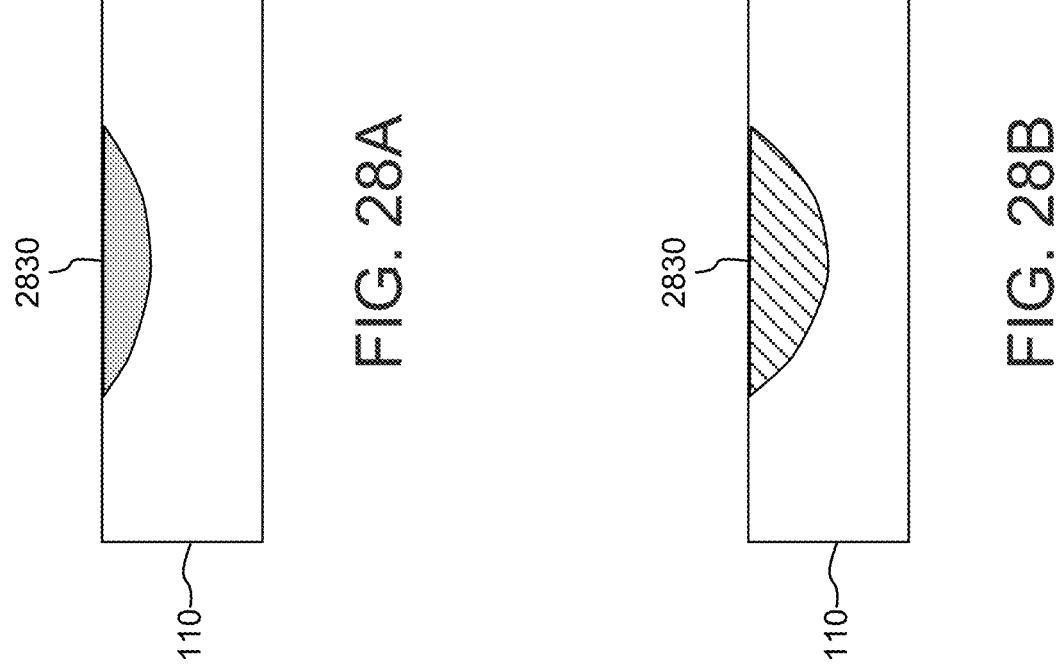
FIG. 28A illustrates a lesion having a first size and/or first optical properties at a first time.
FIG. 28B illustrates a lesion having a second size and/or second optical properties at a second time.

The lesion estimator subsystem 2708 can estimate or determine one or more characteristics of the lesion 130 during a medical procedure. The characteristics of the lesion can include the size, color, and/or other characteristics or properties of the lesion 130. The lesion estimator subsystem 2708 can also be configured to automatically generate a stop signal that causes the ablation catheter to stop epicardial ablation when the lesion 130 has reached a predetermined size, color, and/or characteristics or properties, such as by using artificial intelligence, image recognition, and/or other methods. For example, the lesion estimator 2708 can determine that lesion 2830 has a first size and/or first optical properties at a first time, and that lesion 2830 has a second size and/or second optical properties at a second time, as illustrated in FIGS. 28A and 28B, respectively. In another embodiment, the lesion estimator 2708 can determine a rate of change in the size, optical properties, and/or other characteristics, such as the rate of change between the first and second times in FIGS. 28A and 28B, respectively.

The scar tissue tracker subsystem 2709 can locate and/or track existing scar tissue (e.g., in real time) of the myocardium such as due to previous myocardial infections. The output of the scar tissue tracker subsystem 2709 can be used by the ablation control subsystem 2712 to automatically control ablation such as by adjusting the ablation energy. In addition, the output of the scar tissue tracker subsystem 2709 can be sent to the annotation subsystem 2703 to annotate the detected scar tissue in the displayed image. These annotations can be useful for the operator (e.g., physician) to direct the ablation catheter or other medical instrument to healthy tissue and away from the detected scar tissue. In addition, the operator can use to the scar tissue annotations to manually adjust the ablation energy. The scar tissue annotations can include a graphical overlay (e.g., a colored line such as a red line) and/or a transparent colored filter. The scar tissue tracker subsystem 2709 can use artificial intelligence, image recognition, and/or other methods.

The fat pads tracker subsystem 2710 can locate and/or track epicardial fat pads (e.g., in real time) which may be near the target site. The output of the fat pads tracker subsystem 2710 can be used by the ablation control subsystem 2712 to automatically control ablation such as by adjusting the ablation energy. For example, fat pads are insulators and may require additional energy to ablate. In addition, the output of the fat pads tracker subsystem 2710 can be sent to the annotation subsystem 2703 to annotate the detected fat pads in the displayed image. These annotations can be useful for the operator (e.g., physician) to optionally direct the ablation catheter or other medical instrument away from the fat pads. In addition, the operator can use to the fat pad annotations to manually adjust the ablation energy. For example, performing an ablation on a fat pad generally requires more ablation energy than performing an ablation on other tissue. The fat pad annotations can also be used to improve ablation efficiency. The fat pad annotations can include a graphical overlay (e.g., a colored line such as a red line) and/or a transparent colored filter. The fat pads tracker subsystem 2710 can use artificial intelligence, image recognition, and/or other methods. For example, the fat pads tracker subsystem 2710 can recognize fat pads based on color (e.g., yellow) and/or shape.

The coronary vessel tracker subsystem 2711 can locate and/or track coronary vessels (e.g., in real time) which may be near the target site. The output of the coronary vessel tracker subsystem 2711 can be used by the ablation control subsystem 2712 to automatically control ablation such as by automatically stopping ablation close to a coronary vessel. The ablation of a coronary vessel is generally undesirable and could injure the patient and/or cause undesired complications during the medical procedure. In addition, the output of the coronary vessel tracker subsystem 2711 can be sent to the annotation subsystem 2703 to annotate the detected fat pads in the displayed image. These annotations can be useful for the operator (e.g., physician) to direct the ablation catheter or other medical instrument to away from any coronary vessels to avoid ablating them. The coronary vessel annotations can include a graphical overlay (e.g., a colored line such as a red line) and/or a transparent colored filter. The coronary vessel tracker subsystem 2711 can use artificial intelligence, image recognition, and/or other methods. For example, the coronary vessel tracker subsystem 2711 can recognize coronary vessels based on color (e.g., blue or red) and/or shape.

The ablation control subsystem 2712 can control the intensity, frequency, and/or other settings of the ablation catheter, which can be manually or automatically controlled. The ablation control subsystem 2712 can start and stop ablation in response to a control signal. For example, the ablation control subsystem 2712 can start or stop ablation in response to user input via user interface and control subsystem 2713. Additionally or alternatively, the ablation catheter can include a button that generates a first signal when depressed that causes the ablation control subsystem 2712 to start ablation. When the button is released, a second signal can cause the ablation control subsystem 2712 to stop ablation. The ablation control subsystem 2712 can also stop ablation in response to the stop signal sent from the lesion estimator subsystem 2708.

Figure 22:
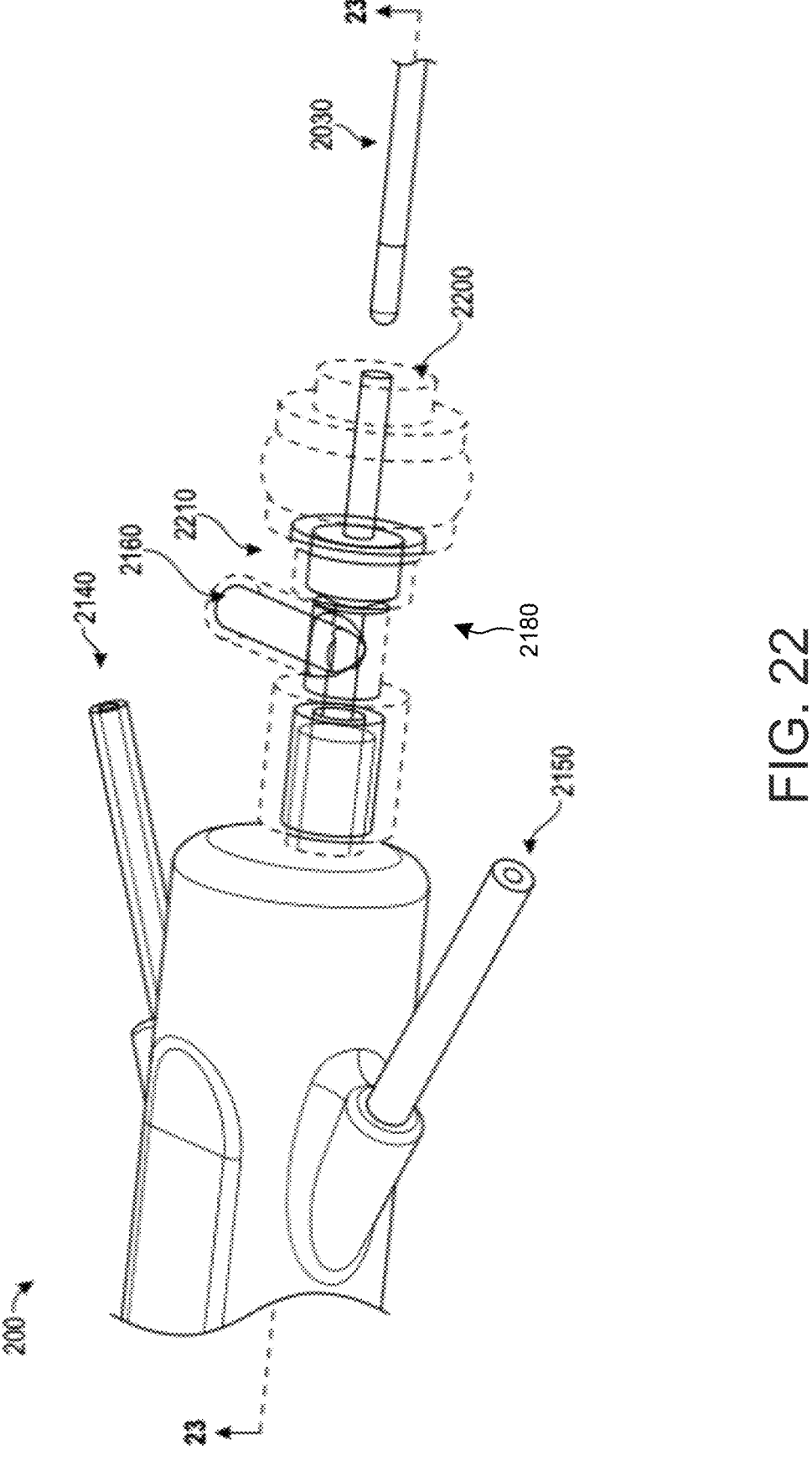
FIG. 22 is a perspective view of a proximal portion of the handle of the instrument port according to an embodiment.

Returning to FIG. 21, a flushing and/or vacuum port 2160 is formed in an adapter 2180 attached to the proximal end of the handle 200. Alternatively, the flushing and/or vacuum port 2160 can be formed in the proximal end of the handle 200 (e.g., similar to ports 2140, 2150. The flushing and/or vacuum port 2160 is fluidly coupled to the fluid channel 2060 and to the vacuum/liquid flush source 2130 for applying a vacuum and/or for introducing a liquid into the fluid channel 2060. The adapter 2180 preferably includes a Tuohy-Borst adapter that can include a working port 2200 through which the medical device 2030 (e.g., ablation catheter) can be inserted into the working channel 320, for example as illustrated in FIG. 22. A valve 2210 can be disposed between flushing and/or vacuum port 2160 and the working port 2200 to direct the liquid and/or vacuum into the working channel 320 as needed. The valve 2210 can be actuated by rotating the adapter 2180.

Figure 23:
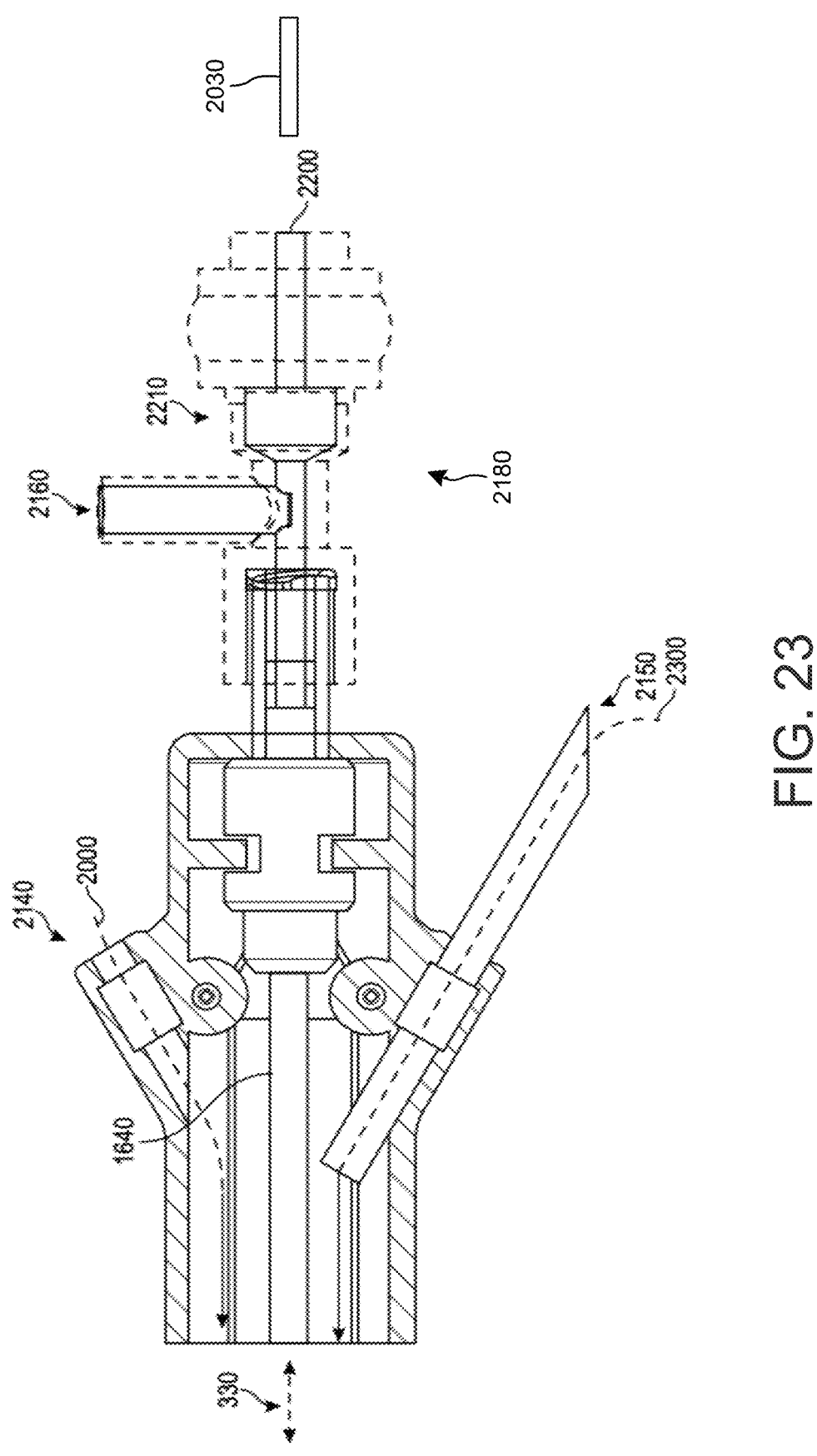
FIG. 23 is a cross-sectional view of a proximal portion of the handle.

FIG. 23 is a cross-sectional view of a proximal portion of the handle 200 through line 23-23 in FIG. 22. The cross section does not include the medical instrument 2030. This figure illustrates an example of how the working tube 1640, fluid tube 2000, and imaging cables 2300 are coupled to respective ports 2200, 2140, 2150 in the handle 200. The imaging cables 2300 can comprise fiber optic cables 2011, 2012 and/or imaging cable 2020.

Figure 24:
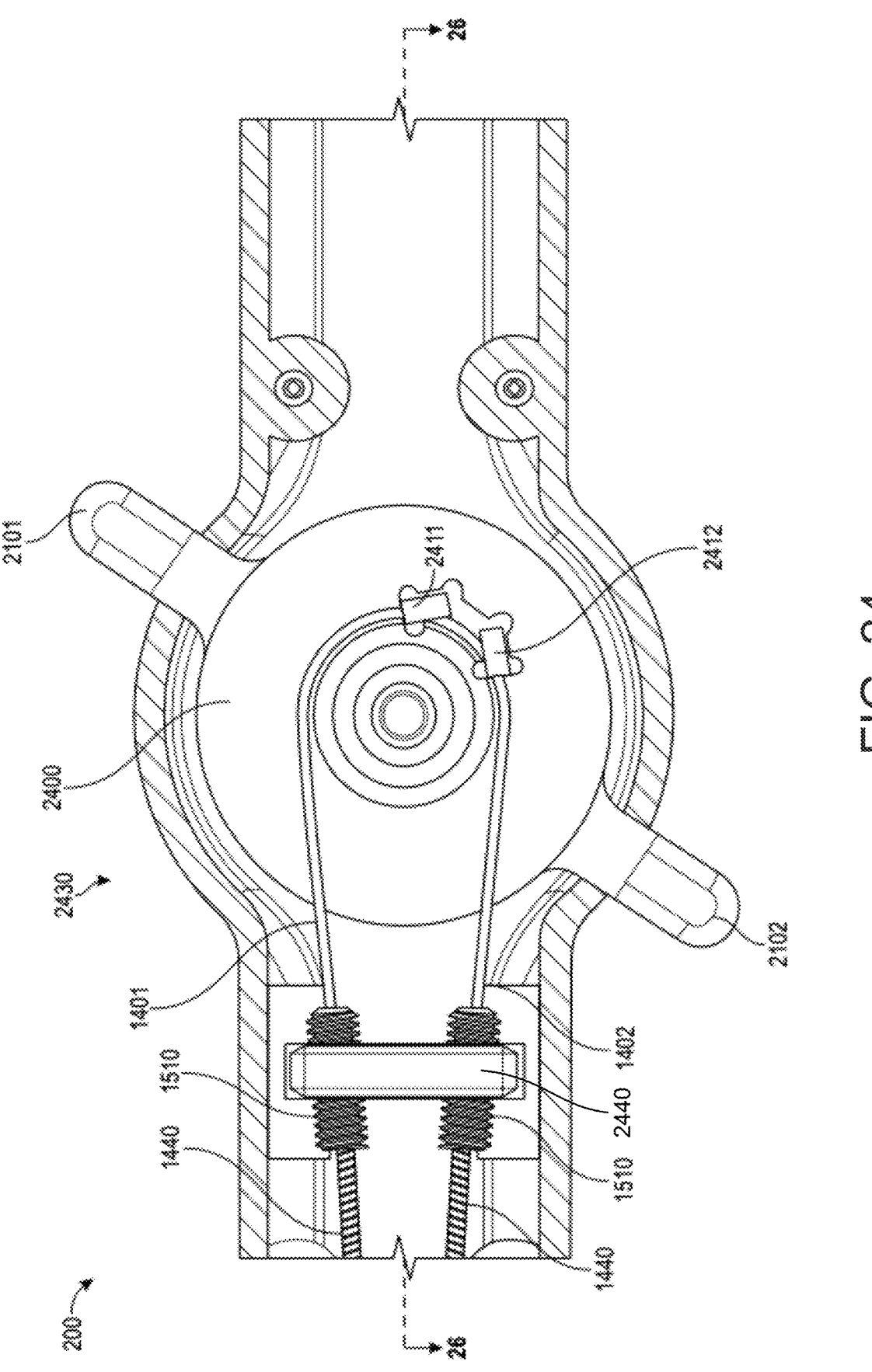
FIG. 24 is a top view of a portion of handle with the housing removed.

FIG. 24 is a top view of a portion of handle 200 with the housing removed to illustrate the structure and operation of the levers 2101, 2102 according to an embodiment. The levers 2101, 2102 are attached to a spindle 2400 on which first and second ends 2411, 2412 of the first and second wires

1401, 1402 are attached to form a tip steering apparatus 2430. In the figure, the first lever 2101 is pressed towards the proximal end 202 which causes the spindle 2400 to rotate clockwise (e.g., in a first direction) to increase tension on the first wire 1401 (e.g., by decreasing its effective length). Rotating the spindle 2400 clockwise also decreases tension on the second wire 1402 (e.g., by increasing its effective length) and causes the second lever 2102 to move towards the distal end 204.

Conversely, pressing the second lever 2102 towards the proximal end 202 causes the spindle 2400 to rotate counterclockwise (e.g., in a second direction) to increase tension on the second wire 1402 (e.g., by decreasing its effective length). Rotating the spindle 2400 counterclockwise also decreases tension on the first wire 1401 (e.g., by increasing its effective length) and causes the first lever 2101 to move towards the distal end 204. As can be seen, the first and second levers 2101, 2102 are mechanically coupled via the spindle 2400 and are out of phase. For example, when the first lever 1401 is pushed in one direction (e.g., towards the distal end 204), the second lever 1402 is pushed in the opposite direction (e.g., towards the proximal end 202) which causes a corresponding increase in tension on the first or second wire 1401, 1402 and a corresponding decrease in tension on the second or first wire 1402, 1401, respectively.

This figure also illustrates the adjuster plate 2440 in the handle 200. The adjuster plate 2440 includes threaded holes that engage the external threads on the tension adjuster 1510. The adjuster plate 2440 is attached to and/or secured in the handle 200. The tension adjuster 1510 can be rotated in a first direction to move towards the proximal end 202 of the instrument port 20 (e.g., toward the spindle 2400) and in a second direction to move towards the distal end 204 of the instrument port 20. Since the tightly-wound coil 1440 is attached to a mechanical ring 1200 and the tension adjuster 1510 (e.g., in counterbore 1520), moving the tension adjuster 1510 in the first direction causes the tension of the corresponding wire 1401, 1402 to increase. Conversely, moving the tension adjuster 1510 in the second direction causes the tension of the corresponding wire 1401, 1402 to decrease.

Figure 25:
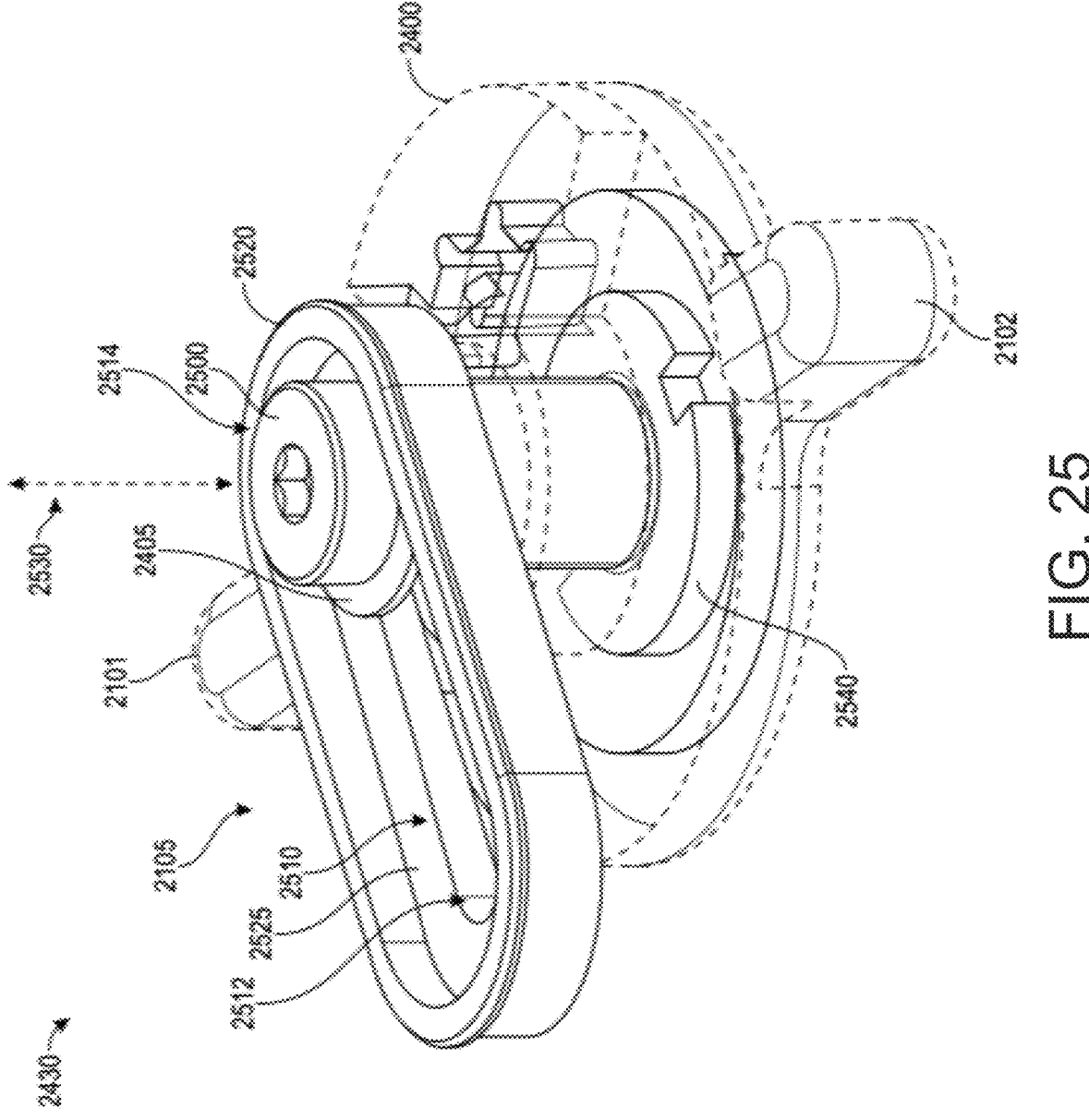
FIG. 25 is an isolated perspective view of the tip steering apparatus illustrated in FIG. 24.

FIG. 25 is an isolated perspective view of the tip steering apparatus 2430 illustrated in FIG. 24. The tip steering apparatus 2430 includes the levers 2101, 2102, the mechanical lock 2105, and the spindle 2400. The wires 1401, 1402 are not illustrated in FIG. 25. The mechanical lock 2105 is mechanically coupled to a shaft 2500 that is slideably coupled to a locking channel 2510 in a locking housing 2420. The external surface 2525 of the locking housing 2520 is relatively higher, as measured with respect to shaft axis 2530, on a locked side 2512 of the locking channel 2510 than on the unlocked side 2514 of the locking channel 2510. An edge 2405 of the shaft 2500 mechanically engages the external surface 2525 of the locking housing 2420. When the shaft 2500 slides to the locked side 2512 of the locking channel 2510, the elevated external surface 2525 creates an upward force on the shaft 2500 to lock the rotation of the spindle 2400 (e.g., by engaging a flared shaft brake 2540). The spindle 2400 is partially transparent in FIG. 25 to further illustrate the tip steering apparatus 2430. In other embodiments, the mechanical lock 2105 can include a push button, a lever, a dial, or other mechanism.

Figure 26:
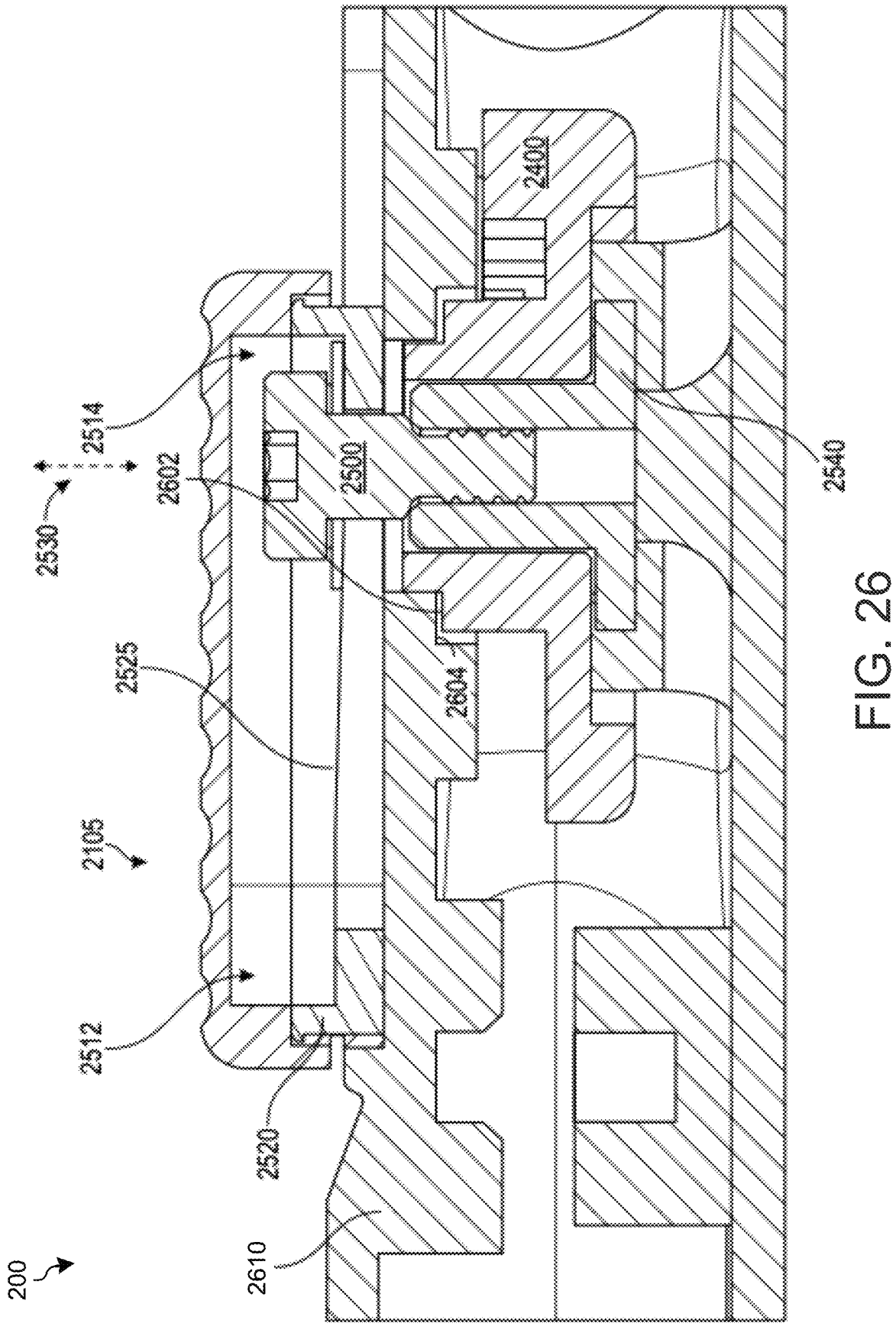
FIG. 26 is a cross-sectional view of a portion of the handle to further illustrate the mechanical lock.

FIG. 26 is a cross-sectional view of a portion of the handle 200 through line 26-26 in FIG. 25 to further illustrate the mechanical lock 2105. The mechanical lock 2105 is in the unlocked state in FIG. 26. In the unlocked state, one or more upper edges 2602 of the spindle 2400 is/are disengaged from one or more inner edges 2604 of the handle 200 to allow the spindle 2400 to rotate freely. In the locked state, the elevated external surface 2525 causes the shaft 2500 to move upwards (e.g., away from the spindle 2400 along shaft axis 2530). The shaft 2500 is mechanically coupled to (e.g., by threads) and/or includes the flared shaft brake 2540, which moves upwards and downwards with the shaft 2500 (e.g., with respect to shaft axis 2530). When the shaft 2500 and flared shaft brake 2540 move upwards to transition the mechanical lock 2105 to the locked state, the flared shaft brake 2510 mechanically engages the spindle 2500 to force the spindle 2500 upwards, which causes the upper edge(s) 2602 of the spindle 2400 to mechanically engage the inner edge(s) 2604 of the handle housing 2610. The mechanical engagement of the upper edge(s) 2602 and the inner edge(s) 2604 increases friction therebetween to mechanically lock the rotation of the spindle 2400. Locking the rotation of the spindle 2400 sets or locks the tension (or lack of tension) on the wires 1401, 1402 to set or lock the bending of the bendable shaft 220 and the customizable angle 1300 of the steerable tip 230 with respect to the elongated shaft 210.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An instrument port comprising:

an elongated shaft having proximal and distal ends and extending along a shaft axis, the elongated shaft having a fluid port defined in an external surface at the distal end of the elongated shaft;

a bendable shaft having a proximal end attached to the distal end of the elongated shaft along the shaft axis, the bendable shaft configured to bend only within a pivot plane that is defined by the shaft axis and a pivot axis that is orthogonal to the shaft axis, the bendable shaft further comprising a plurality of mechanical rings disposed along the shaft axis, each of the plurality of mechanical rings coupled to another of the mechanical rings by a pair of mechanical links, wherein each of the pair of mechanical links comprise a first mechanical link having an interior surface dynamically coupled to an exterior surface of a second mechanical link;

a steerable tip attached to a distal end of the bendable shaft, the steerable tip including an imaging system that includes:

a camera disposed at a distal end of the steerable tip; and a light emitter disposed at the distal end of the steerable tip;

an offset balloon attached to the external surface of the elongated shaft, the offset balloon having an internal volume in fluid communication with the fluid port, the offset balloon having an inflated state and a deflated state, wherein in the inflated state the offset balloon creates space between the elongated shaft and an anatomical feature to permit the bendable shaft to bend within the pivot plane, and wherein the mechanical links mechanically restrict a bending direction of the bendable shaft to the pivot plane;

a handle attached to the proximal end of the elongated shaft, the handle including a spindle in mechanical communication with the bendable shaft to adjust a customizable angle of the steerable tip, the customizable angle measured between the shaft axis and the tip axis;

a mechanical lock having a locked state and an unlocked state, wherein the customizable angle of the steerable tip is locked while the mechanical lock is in the locked state, the mechanical lock comprising:

a shaft comprising a locking shaft axis extending through the spindle and threads configured to couple to a flared shaft brake, the flared shaft brake configured to engage the spindle while in the locked state and to disengage the spindle while in the unlocked state;

a locking housing comprising a locking channel slidably coupled to the shaft, the locking channel comprising:

a locked side; and an unlocked side;

wherein the locking channel transitions between the locked state and the unlocked state by sliding linearly in a direction perpendicular to the locking shaft axis, wherein the mechanical lock is in the locked state when the shaft slides to the locked side, and wherein the mechanical lock is in the unlocked state when the shaft slides to the unlocked side;

a fluid tube disposed in the elongated shaft, the fluid tube fluidly coupled to the fluid port;

a working tube disposed in the elongated shaft, the working tube forming a working channel;

an ablation catheter disposed in the working channel, the ablation catheter configured to form a lesion at a surgical site; and a microprocessor-based controller in electrical communication with the imaging system, the microprocessor-based controller configured to:

acquire image data of the surgical site from the camera associated with a plurality of images;

analyze, using an image processor, the image data of the surgical site from the camera by comparing the image data of the plurality of images to a second of the plurality of images;

automatically detect, in real time, the lesion formed at the surgical site; and automatically stop the ablation catheter when the lesion has a predetermined characteristic;

wherein the predetermined characteristic is derived from the image data of the surgical site.

2. The instrument port of claim 1, wherein the microprocessor based controller further comprises a lesion estimator subsystem, wherein the predetermined characteristic comprises a predetermined size and the lesion comprises a first size detected in a first of the plurality of images and a second size detected in a second of the plurality of images, wherein the lesion estimator subsystem is operative to determine a rate of change in lesion size between the first and second sizes.

3. The instrument port of claim 1, wherein the predetermined characteristic comprises a predetermined color.

4. The instrument port of claim 1, wherein:

the customizable angle is within a range of 0° to 90°, and when the bendable shaft is in an unbent state:

the bendable shaft extends along the shaft axis, and the customizable angle is 0°.

5. The instrument port of claim 1, wherein in the inflated state, the offset balloon is radially asymmetrically inflated, wherein the offset balloon is inflated more on a first side of the shaft axis than on a second side of the shaft axis.

6. The instrument port of claim 1, wherein:

an internal diameter of the working channel is greater than an external diameter of the ablation catheter, and a fluid channel is defined between the internal diameter of the working channel and the external diameter of the ablation catheter.

7. The instrument port of claim 6, wherein the fluid channel is fluidly coupled to a flush liquid source or to a vacuum source.

8. The instrument port of claim 1, wherein the ablation catheter comprises an RF ablation catheter.

9. The instrument port of claim 1, wherein the working tube comprises a flexible cylinder.

10. The instrument port of claim 9, wherein the flexible cylinder comprises a wire-reinforced liner.

11. The instrument port of claim 10, wherein the wire-reinforced liner comprises a tube body comprising fluorinated ethylene propylene and a spiral wire, and wherein an internal surface of the flexible cylinder comprises only the tube body to form a smooth surface to receive the medical instrument.

12. The instrument port of claim 1, wherein:

the elongated shaft comprises a metal tube having an internal surface and an external surface, and a pattern of slits is defined in the elongated shaft to increase a shaft flexibility.

13. The instrument port of claim 12, wherein the metal tube comprises stainless steel.

14. The instrument port of claim 12, wherein the pattern of slits is laser cut.

15. The instrument port of claim 12, wherein the pattern of slits comprises an interrupted spiral.

16. The instrument port of claim 12, wherein:

the pattern of slits comprises a plurality of fins that extend circumferentially on first and second sides of the metal tube, and the plurality of fins on the first side and the plurality of fins on the second side are separated by first and second gaps, the first and second gaps extending along a plane defined by the shaft axis and an axis orthogonal to the shaft axis.

17. The instrument port of claim 1, wherein the spindle comprises a first lever and a second lever, wherein pressing the first lever toward the proximal end causes the spindle to rotate in a first direction, wherein pressing the second lever toward the proximal end causes the spindle to rotate in a second direction, and wherein rotating the spindle in the first direction or the second direction adjusts the customizable angle.

18. The instrument port of claim 1, wherein the locking housing further comprises an external surface traversing a length of the locking channel, wherein the external surface comprises an elevated external surface being higher on the locked side of the locking channel than on the unlocked side of the locking channel relative the locking shaft axis, and wherein sliding the shaft to the locked side causes the elevated external surface to create an upward force on the shaft so that the shaft moves upward to engage the flared shaft brake with the spindle to enter the locked state.

19. An instrument port comprising:

an elongated shaft having proximal and distal ends and extending along a shaft axis, the elongated shaft having a fluid port defined in an external surface at the distal end of the elongated shaft;

a bendable shaft having a proximal end attached to the distal end of the elongated shaft along the shaft axis, the bendable shaft configured to bend only within a pivot plane that is defined by the shaft axis and a pivot axis that is orthogonal to the shaft axis;

a steerable tip attached to a distal end of the bendable shaft, the steerable tip including an imaging system that includes:

a camera disposed at a distal end of the steerable tip; and an offset balloon attached to the external surface of the elongated shaft, the offset balloon having an internal volume in fluid communication with the fluid port, the offset balloon having an inflated state and a deflated state;

a handle attached to the proximal end of the elongated shaft, the handle including a spindle in mechanical communication with the bendable shaft to adjust a customizable angle of the steerable tip, the customizable angle measured between the shaft axis and the tip axis; and a mechanical lock having a locked state and an unlocked state, wherein the customizable angle of the steerable tip is locked while the mechanical lock is in the locked state, the mechanical lock comprising:

a shaft comprising a locking shaft axis extending through the spindle and threads configured to couple to a flared shaft brake, the flared shaft brake configured to engage the spindle while in the locked state and to disengage the spindle while in the unlocked state;

a locking housing comprising a locking channel slidably coupled to the shaft, the locking channel comprising:

a locked side; and an unlocked side;

wherein the locking channel transitions between the locked state and the unlocked state by sliding linearly in a direction perpendicular to the locking shaft axis, wherein the mechanical lock is in the locked state when the shaft slides to the locked side, and wherein the mechanical lock is in the unlocked state when the shaft slides to the unlocked side.

20. The instrument port of claim 18, wherein the flared shaft brake encircles the shaft, and wherein the engagement of the flared shaft brake with the spindle causes the spindle to move upwards causing upper edges of the spindle to mechanically engage inner edges of the locking housing to increase friction therebetween.

* * * * *